(12) United States Patent
Nakadate et al.

(10) Patent No.: US 11,627,956 B2
(45) Date of Patent: Apr. 18, 2023

(54) AUTOMATIC NEEDLE MOVER

(71) Applicants: KYUSHU UNIVERSITY, NATIONAL UNIVERSITY CORPORATION, Fukuoka (JP); NIPPON MEDICAL SCHOOL FOUNDATION, Tokyo (JP)

(72) Inventors: Ryu Nakadate, Fukuoka (JP); Susumu Oguri, Fukuoka (JP); Makoto Hashizume, Fukuoka (JP); Akio Morita, Tokyo (JP)

(73) Assignees: KYUSHU UNIVERSITY, NATIONAL UNIVERSITY CORPORATION, Fukuoka (JP); NIPPON MEDICAL SCHOOL FOUNDATION, Tokyo (JP)

( * ) Notice: Subject to any disclaimer, the term of this patent is extended or adjusted under 35 U.S.C. 154(b) by 346 days.

(21) Appl. No.: 17/059,328

(22) PCT Filed: May 30, 2019

(86) PCT No.: PCT/JP2019/021590
§ 371 (c)(1),
(2) Date: Nov. 27, 2020

(87) PCT Pub. No.: WO2019/230906
PCT Pub. Date: Dec. 5, 2019

(65) Prior Publication Data
US 2021/0228205 A1 Jul. 29, 2021

(30) Foreign Application Priority Data
May 31, 2018 (JP) .............................. JP2018-104506

(51) Int. Cl.
*A61B 17/04* (2006.01)
*A61B 17/062* (2006.01)

(52) U.S. Cl.
CPC ...... *A61B 17/0491* (2013.01); *A61B 17/0483* (2013.01); *A61B 17/062* (2013.01)

(58) Field of Classification Search
CPC ............ A61B 17/0491; A61B 17/0483; A61B 17/062; A61B 2017/2927; A61B 2017/2944
See application file for complete search history.

(56) References Cited

U.S. PATENT DOCUMENTS

2009/0177031 A1* 7/2009 Surti .................. A61B 1/00087
606/139
2010/0087838 A1 4/2010 Nobles et al.
2012/0277768 A1 11/2012 Viola et al.

FOREIGN PATENT DOCUMENTS

| JP | 2000-037391 A | 2/2000 |
| JP | 5421927 B2 | 2/2014 |
| WO | 2009/089101 A2 | 7/2009 |

OTHER PUBLICATIONS

International Search Report issued in PCT/JP2019/021590; dated Aug. 20, 2019, p. 1.

(Continued)

*Primary Examiner* — Kelly J Bekker
*Assistant Examiner* — Mohammed S Adam
(74) *Attorney, Agent, or Firm* — Studebaker & Brackett PC

(57) ABSTRACT

An automatic needle mover for moving a medical threaded needle includes: two shafts extending in the same direction and slidable relative to each other along a longitudinal direction; a needle-holding portion provided on one end side of the second shaft; a needle-receiving portion provided on one end side of the first shaft; and a handle serving as a control portion for controlling the sliding of the two shafts. The needle-holding portion has a first claw portion protruding in a direction intersecting the longitudinal direction of (Continued)

the shafts. The needle-receiving portion has a second claw portion protruding in a direction intersecting the longitudinal direction of the shafts. As a result of the sliding of the two shafts, the needle-holding portion and the needle-receiving portion become close to each other and a straight needle held by the needle-holding portion can be press-fitted into the needle-receiving portion.

7 Claims, 15 Drawing Sheets

(56) References Cited

OTHER PUBLICATIONS

Notification of Transmittal of Translation of the International Preliminary Report on Patentability and Translation of Written Opinion of the International Searching Authority; PCT/JP2019/021590 ; dated Dec. 10, 2020, pp. 1-7.

* cited by examiner

*Fig.10*
(a)
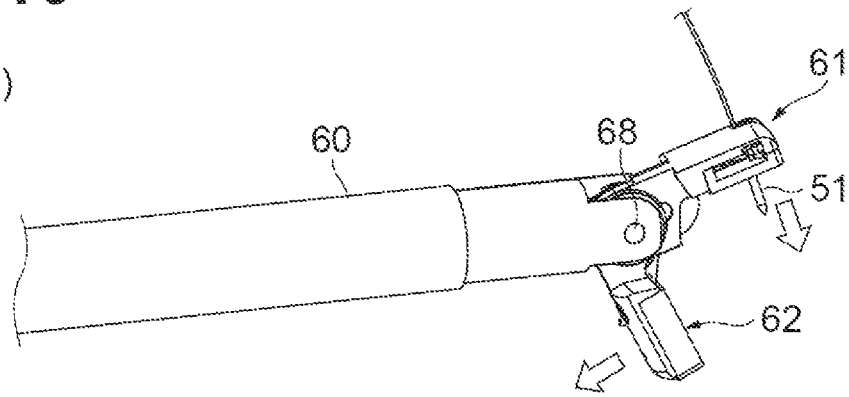
(b)
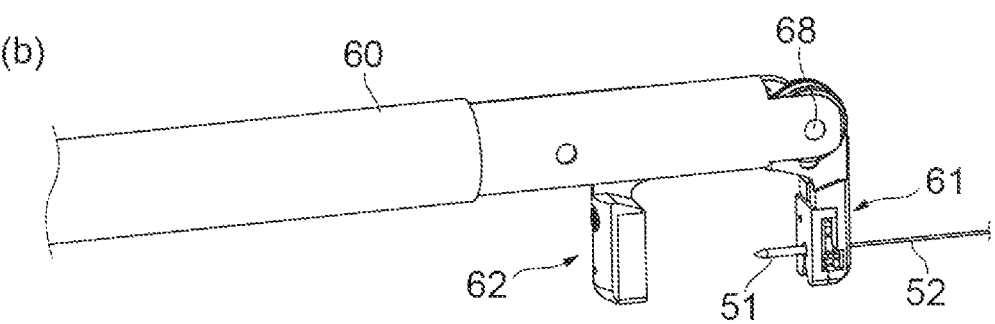
(c)
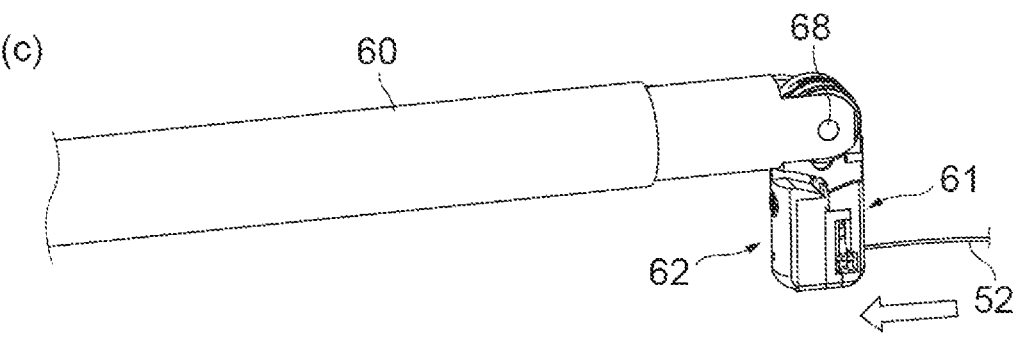
(d)
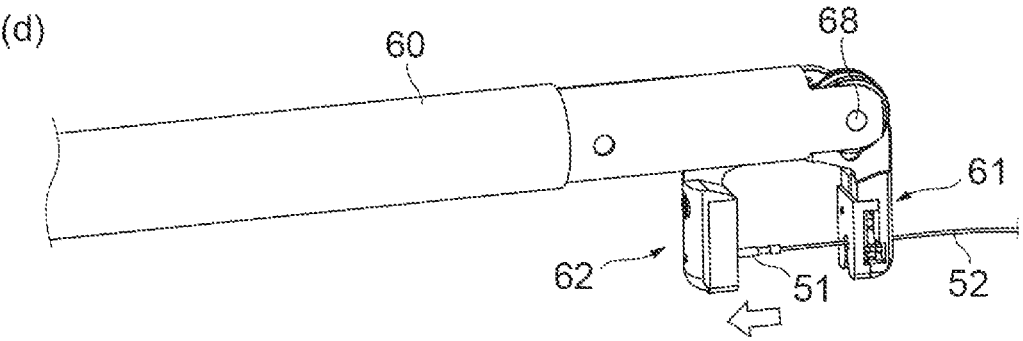

AUTOMATIC NEEDLE MOVER

TECHNICAL FIELD

The present invention relates to an automatic needle mover.

BACKGROUND ART

Patent Literature 1 discloses a guide tool that has a pair of jaws and delivers a medical needle with thread held in a needle stand portion of a first jaw to a needle-receiving portion of a second jaw as an instrument for moving a medical needle with thread used for suturing an affected area or the like. The pair of jaws are disposed so as to face each other in a direction intersecting the longitudinal direction of the guide tool, and thus the tool is preferably used in the case of a suture surface extending in the same direction as the longitudinal direction of the guide tool.

CITATION LIST

Patent Literature

Patent Literature Japanese Unexamined Patent Publication No. 2000-37391

SUMMARY OF INVENTION

Technical Problem

However, in the case of a suture surface extending along a surface intersecting the longitudinal direction of the guide tool, it may be difficult to move the needle for suturing with the guide tool described in Patent Literature 1.

The present invention has been made in view of the above, and an object of the present invention is to provide an automatic needle mover capable of moving a medical needle with thread on a suture surface intersecting the longitudinal direction of the instrument.

Solution to Problem

In order to achieve the above object, the automatic needle mover according to one form of the present invention is an automatic needle mover for moving a medical threaded needle including a straight needle and a thread connected to the straight needle. The automatic needle mover includes two shafts extending in the same direction and slidable relative to each other along a longitudinal direction, a needle holding portion provided on one end side of a first shaft as one of the two shafts, a needle-receiving portion provided on one end side of a second shaft as the other shaft, and a control portion for controlling the sliding of the two shafts, the control portion being provided on a side opposite to the end side where the needle holding portion and the needle-receiving portion are provided when viewed in the longitudinal direction. The needle holding portion has a first claw portion protruding in a direction intersecting the longitudinal direction of the first shaft in an end portion of the first shaft and a first groove portion provided in the first claw portion and including a region having a width smaller than a diameter of the straight needle and larger than a diameter of the thread. The needle-receiving portion has a second claw portion protruding in a direction intersecting the longitudinal direction of the second shaft in an end portion of the second shaft and a second groove portion provided in the second claw portion and having a width at which the straight needle can be inserted by elasticity of the second claw portion and the straight needle can be held by friction with the straight needle when the straight needle is inserted along the longitudinal direction. The needle holding portion and the needle-receiving portion become close to each other and the straight needle held by the needle holding portion can be press-fitted into the needle-receiving portion as a result of the sliding of the two shafts.

In the automatic needle mover described above, the needle holding portion and the needle-receiving portion become close to each other as a result of the sliding of the two shafts and the straight needle held by the needle holding portion can be press-fitted into the needle-receiving portion by the shaft sliding control by means of the control portion. In addition, the needle holding portion has the first groove portion provided in the first claw portion and including the region having the width smaller than the diameter of the straight needle and larger than the diameter of the thread and the needle-receiving portion is provided in the second claw portion and has the width at which the straight needle can be inserted by the elasticity of the second claw portion and the straight needle can be held by the friction with the straight needle when the straight needle is inserted along the longitudinal direction. In such a configuration, the straight needle held by the needle holding portion can be delivered to the needle-receiving portion by the needle holding portion and the needle-receiving portion becoming close to each other as a result of the sliding of the two shafts. By the needle movement being performed by means of the straight needle delivery between the needle holding portion and the needle-receiving portion, the medical threaded needle can be moved on a suture surface that intersects the longitudinal direction of the instrument.

Here, an aspect can be adopted in which the needle-receiving portion is farther from the control portion than the needle holding portion along the longitudinal direction of the two shafts.

By the aspect being adopted in which the needle-receiving portion is farther from the control portion than the needle holding portion along the longitudinal direction of the two shafts, the straight needle can be moved in a direction away from the control portion by means of the straight needle delivery from the needle holding portion to the needle-receiving portion.

In addition, an aspect can be adopted in which the second groove portion has a narrow portion with a smallest width in a middle when viewed along the longitudinal direction.

By the second groove portion provided in the needle-receiving portion having the narrow portion, the straight needle inserted in the second groove portion receives the greatest friction and is supported in the narrow portion. Accordingly, the straight needle supported in the needle-receiving portion is pivotable about the narrow portion. In such a structure, the straight needle is freely pivotable when the automatic needle mover is moved, and thus a decline in work efficiency can be prevented even in a case where the place where the automatic needle mover is operable is narrow.

In addition, an aspect can be adopted in which the needle-receiving portion is closer to the control portion than the needle holding portion along the longitudinal direction of the two shafts.

By the aspect being adopted in which the needle holding portion is farther from the control portion than the needle-receiving portion along the longitudinal direction of the two shafts, the straight needle can be moved in a direction of approach from the control portion by means of the straight needle delivery from the needle holding portion to the needle-receiving portion.

In addition, an aspect can be adopted in which the needle-receiving portion has a pair of corner portions formed by an end surface of the second claw portion and the second groove portion in an end portion of the second groove portion on a side where the straight needle is inserted, an angle of the end portion abutting against the straight needle being 90° or an acute angle in a plan view.

By the pair of corner portions being provided in the second claw portion and the angle of the end portion abutting against the straight needle being 90° or an acute angle as described above, tissue or the like around the straight needle can be prevented from being caught in the second groove portion when the straight needle is inserted into the second groove portion.

In addition, an aspect can be adopted in which the two shafts are connected by a link member provided at both ends with a first shaft serving as an axis for pivoting with respect to the first shaft and a second shaft serving as an axis for pivoting with respect to the second shaft and the needle-receiving portion moves in a substantially circular arc-shaped trajectory with respect to the needle holding portion as a result of the sliding of the two shafts.

By the above configuration being adopted, the needle-receiving portion can be moved in a substantially circular arc-shaped trajectory with respect to the needle holding portion. Accordingly, even if the direction of the straight needle supported in the needle holding portion is different from, for example, the longitudinal direction of the two shafts, the needle-receiving portion can be moved in accordance with the direction of the straight needle and the straight needle can be moved.

In addition, the needle-receiving portion and the needle holding portion are pivotable about a pivot shaft as an axis, the pivot shaft being provided in the end portions of the two shafts on the side where the needle-receiving portion and the needle holding portion are provided and extending in a direction intersecting the longitudinal direction, and a positional relationship between the needle-receiving portion and the needle holding portion along the longitudinal direction of the two shafts is reversed as a result of the pivoting about the pivot shaft as an axis.

In the case of the above configuration in which the needle-receiving portion and the needle holding portion are provided in the end portions of the two shafts and are pivotable about the pivot shaft as an axis extending in the direction intersecting the longitudinal direction and the positional relationship between the needle-receiving portion and the needle holding portion along the longitudinal direction of the two shafts is reversed as a result of the pivoting, the automatic needle mover is capable of realizing both a straight needle movement away from the control portion and a straight needle movement toward the control portion. Accordingly, work efficiency is improved.

Advantageous Effects of Invention

According to the present invention, an automatic needle mover capable of moving a medical threaded needle on a suture surface intersecting the longitudinal direction of the instrument is provided.

BRIEF DESCRIPTION OF DRAWINGS

FIG. 10 is a diagram describing threaded needle delivery in the automatic needle mover.

DESCRIPTION OF EMBODIMENTS

Figure 1:
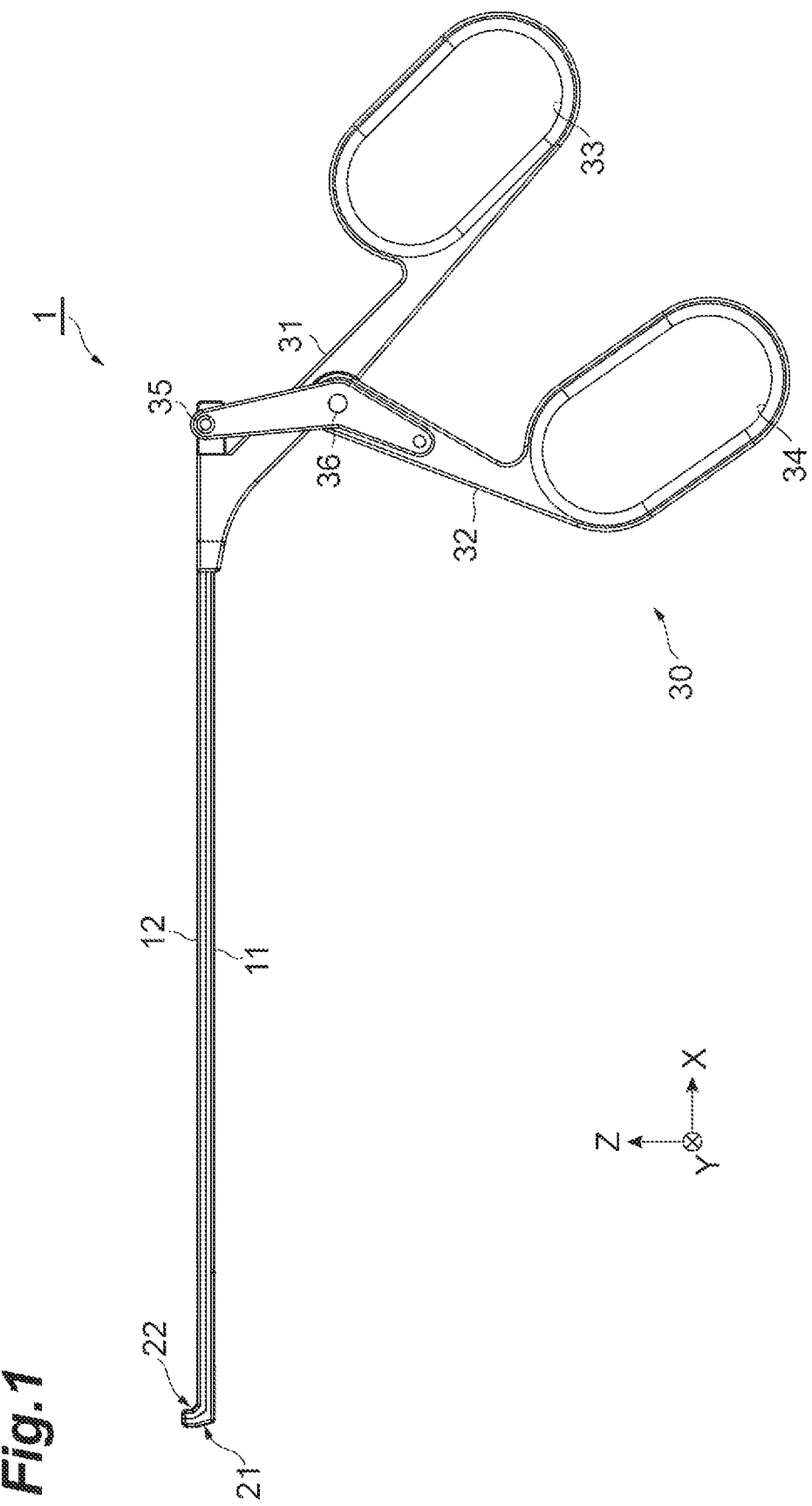
FIG. 1 is a side view of the automatic needle mover according to a first embodiment of the present invention.

Hereinafter, embodiments of the present invention will be described in detail with reference to the accompanying drawings. It should be noted that the same elements are denoted by the same reference numerals and redundant description is omitted in the description of the drawings.

First Embodiment

Figure 2:
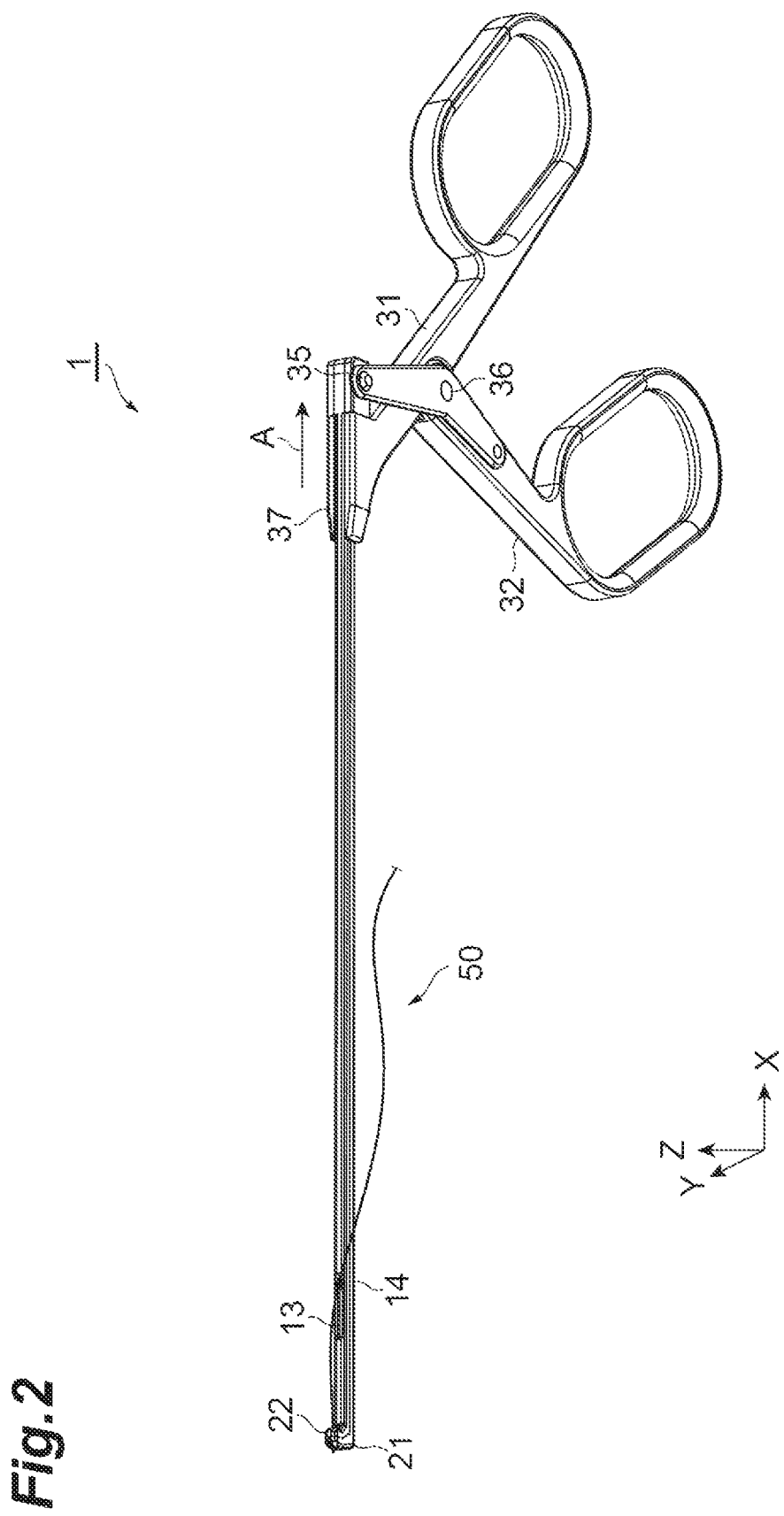
FIG. 2 is a perspective view of the automatic needle mover according to the first embodiment.
Figure 3:
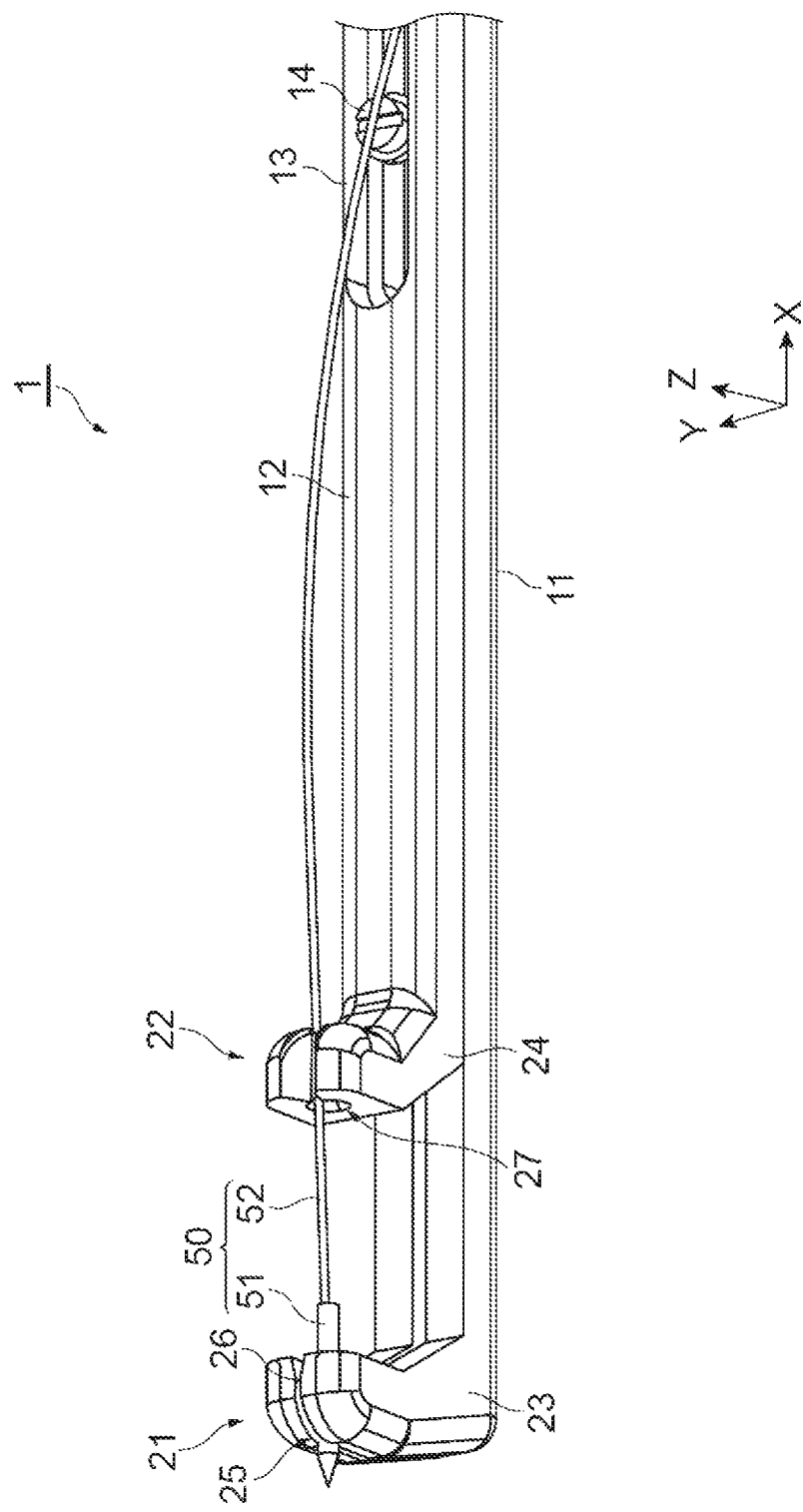
FIG. 3 is a perspective view of the tip part of the automatic needle mover.
Figure 4:
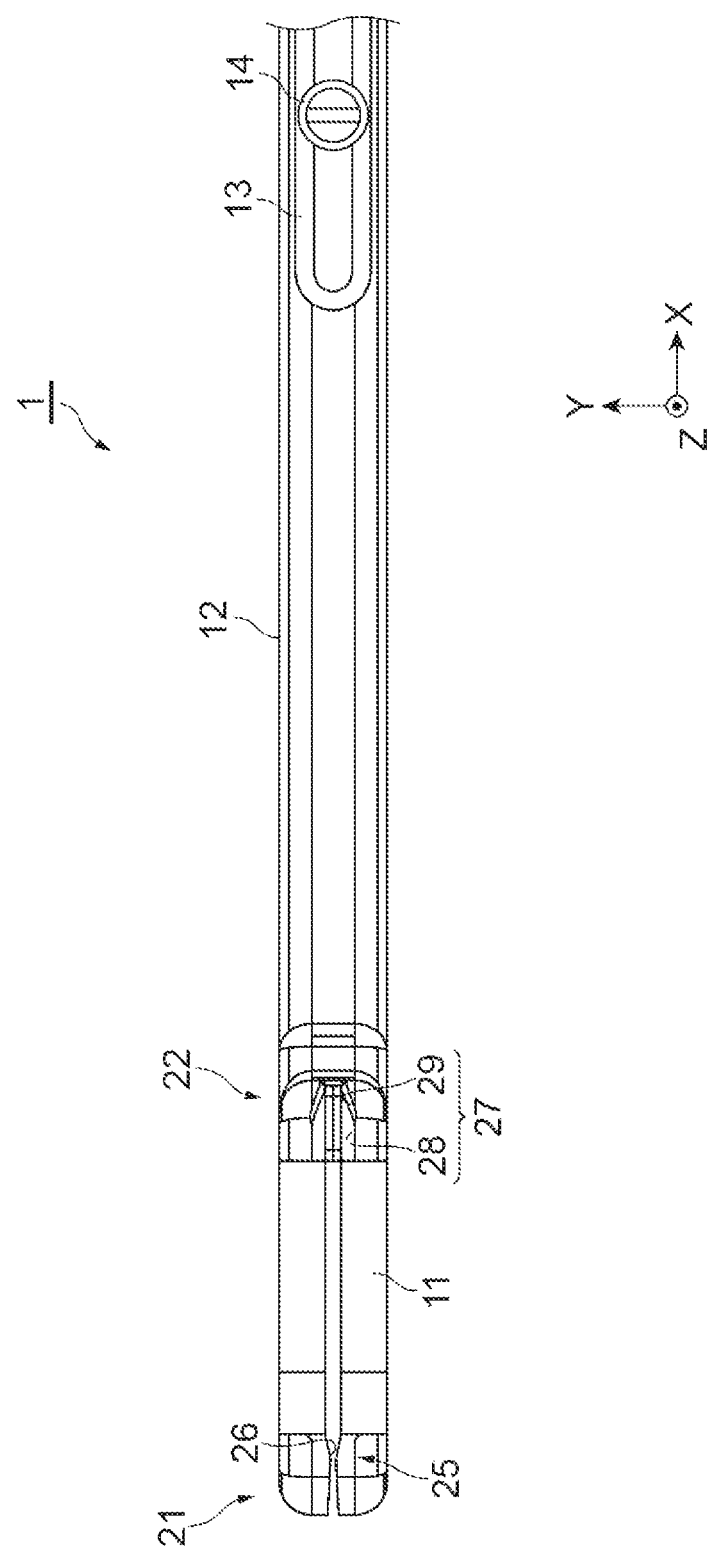
FIG. 4 is a plan view of the tip part of the automatic needle mover.

FIG. 1 is a side view of the automatic needle mover according to a first embodiment of the present invention, and FIG. 2 is a perspective view of the automatic needle mover according to the first embodiment. In addition, FIG. 3 is a perspective view of the tip part of the automatic needle mover and FIG. 4 is a plan view of the tip part. For convenience of description, an XYZ coordinate system is illustrated in FIGS. 1 to 4. An automatic needle mover 1 described in the first embodiment is used when target tissue or the like is sutured by means of a medical threaded needle. Examples of the target tissue include the deep brain, and the automatic needle mover 1 is used when deep brain tissue is sutured via the nasal cavity. However, the tissue to be sutured is not limited to the above. In addition, although the automatic needle mover described in the following embodiment is used in the field of neurosurgery, otorhinology, or ophthalmology, the field of use is not limited thereto.

As illustrated in FIGS. 1 and 2, the automatic needle mover 1 has a first shaft 11 (second shaft) having a first needle support portion 21 at the tip thereof and a second shaft 12 (first shaft) having a second needle support portion 22 at the tip thereof. The two shafts, that is, the first shaft 11 and the second shaft 12 extend in the same direction (X-axis direction), and the second shaft 12 is slidable along the direction of extension (X-axis direction) with respect to the first shaft 11.

In addition, the first needle support portion 21 protrudes in a direction intersecting the direction of extension of the first shaft 11 (Z-axis positive direction in the case of the automatic needle mover 1). In addition, the second needle support portion 22 protrudes in the direction that intersects the direction of extension of the second shaft 12 and is the same as the direction of protrusion of the first needle support portion 21 (Z-axis positive direction in the case of the automatic needle mover), As a result, the relative positional relationship between the first needle support portion 21 and the second needle support portion 22 changes by the second shaft 12 sliding with respect to the first shaft 11. FIG. 1 illustrates a state where the first needle support portion 21 and the second needle support portion 22 abut against each other. The first needle support portion 21 and the second needle support portion 22 have a function of supporting a medical threaded needle (medical needle with thread), details of which will be described later.

The automatic needle mover 1 has a handle 30 for sliding the second shaft 12 with respect to the first shaft 11. The handle 30 functions as a control portion for controlling the sliding of the first shaft 11 and the second shaft 12, The handle 30 includes a first handle 31 and a second handle 32. The first handle 31 is attached to one end side of the first shaft 11 (side opposite to the end portion side where the first needle support portion 21 is provided) and has an opening 33 into which a user of the automatic needle mover 1 inserts a finger in order to operate the first handle 31. In addition, the second handle 32 is pivotably and axially supported by a shaft 35 with respect to one end side of the second shaft 12 (side opposite to the end portion side where the second needle support portion 22 is provided). Further, the second handle 32 is pivotably and axially supported by a shaft 36 with respect to the first handle 31 and has an opening 34 into which the user of the automatic needle mover 1 inserts a finger in order to operate the second handle 32.

As illustrated in FIG. 2, the first handle 31 that is fixed to the first shaft 11 has a groove portion 37 extending along the sliding direction of the second shaft 12 (longitudinal direction of the second shaft 12: X-axis direction). The second shaft 12 is connected to the second handle 32 so as to be slidable with respect to the first shaft 11 in a state where a part of the second shaft 12 is accommodated in the groove portion 37. Further, as illustrated in FIG. 2, the second shaft 12 is provided with an opening 13 along the longitudinal direction while the first shaft 11 is provided with a protrusion 14 at a position allowing insertion into the opening 13 (see also FIGS. 3 and 4).

In the automatic needle mover 1 described above, the second handle 32 pivots about the shaft 36 when the second handle 32 is operated so as to be separated from the first handle 31. As a result, the second shaft 12 axially supported via the shaft 35 with respect to the second handle 32 slides along the sliding direction (longitudinal direction of the second shaft 12: X-axis direction). By the second handle 32 being operated so as to be separated from the first handle 31, the end portion of the second handle 32 on the side opposite to the side where the opening 34 is provided (side where the shaft 35 is provided) moves in the arrow A direction illustrated in FIG. 2 (X-axis positive direction). As a result, the second shaft 12 connected to the second handle 32 via the shaft 35 also slides in the arrow A direction. As a result, the second needle support portion 22 provided at the tip of the second shaft 12 is separated from the first needle support portion 21 provided at the tip of the first shaft 11.

On the other hand, the second handle 32 pivots about the shaft 36 and the second shaft 12 axially supported via the shaft 35 with respect to the second handle 32 slides along the sliding direction (longitudinal direction of the second shaft 12: X-axis direction) when the second handle 32 is operated so as to approach the first handle 31. By the second handle 32 being operated so as to approach the first handle 31, the end portion of the second handle 32 on the side opposite to the side where the opening 34 is provided moves in the direction opposite to the arrow A direction illustrated in FIG. 2 (X-axis negative direction). As a result, the second shaft 12 connected to the second handle 32 via the shaft 35 also slides in the direction opposite to the arrow A direction. As a result, the second needle support portion 22 provided at the tip of the second shaft 12 approaches and abuts against the first needle support portion 21 provided at the tip of the first shaft 11.

It should be noted that the direction of movement of the second shaft 12 with respect to the first shaft 11 is regulated by the second shaft 12 being accommodated in the groove portion 37 provided in the first handle 31 and the protrusion 14 of the first shaft 11 being inserted in the opening 13 provided in the second shaft 12. As a result, the second shaft 12 slides with respect to the first shaft 11 such that the sliding direction is the longitudinal direction of the second shaft 12.

Although the sliding of the second shaft 12 to the side of the first needle support portion 21 of the first shaft 11 is regulated by, for example, the abutting between the first needle support portion 21 and the second needle support portion 22 and the abutting of the first handle 31 against the groove portion 37 by the second shaft 12, methods for the regulation are not particularly limited. In addition, although the sliding of the second shaft 12 to the side away from the first needle support portion 21 of the first shaft 11 is regulated by the movable range of the second shaft 12 at a time when the second handle 32 is pivoted in a state of accommodation in the groove portion 37, methods for the regulation are not particularly limited.

The material of the automatic needle mover 1 including the first shaft 11 and the second shaft 12 is not particularly limited insofar as the material does not affect the tissue for which the automatic needle mover 1 is used, and stainless steel, a titanium alloy, or the like can be used. In addition, a material that can be washed, disinfected, or sterilized and is commonly used as, for example, a material for surgical instruments can be used. In addition, there is no need to use the same material for the entire automatic needle mover 1 and, for example, only the first shaft 11 and the second shaft 12 may be made of the material described above.

The lengths of the first shaft 11 and the second shaft 12 are not particularly limited insofar as the first shaft 11 and the second shaft 12 are long enough to reach the tissue for which the automatic needle mover 1 is used, and the lengths can be appropriately selected in accordance with the physique of, for example, a patient who has the tissue for which the automatic needle mover 1 is used, the positional relationship between the tissue to be sutured and the operator of the automatic needle mover 1, and so on. In a case where the automatic needle mover 1 is used for deep brain suturing via the nasal cavity, the lengths of the first shaft 11 and the second shaft 12 can be, for example, approximately 150 mm to 170 mm. Further, the cross-sectional shapes of the first shaft 11 and the second shaft 12 are not particularly limited and the shapes can be, for example, quadrangular. In addition, the combined outer diameter of the first shaft 11 and the second shaft 12 is not particularly limited insofar as the outer diameter allows the tissue for which the automatic needle mover 1 is used to be reached and the outer diameter can be appropriately selected in accordance with the physique of, for example, the patient who has the tissue for which the automatic needle mover 1 is used and so on. In a case where the automatic needle mover 1 is used for deep brain suturing via the nasal cavity, the combined outer diameter of the first shaft 11 and the second shaft can be, for example, approximately 2 mm to 3 mm.

In the automatic needle mover 1, medical threaded needle delivery is performed between the first needle support portion 21 and the second needle support portion 22 by the sliding of the second shaft 12 with respect to the first shaft 11 being used. This point will be described with reference to FIGS. 3 and 4.

A threaded needle 50 (medical threaded needle) that can be used in the automatic needle mover 1 will be described first. As illustrated in the drawings including FIG. 3, the threaded needle 50 has a needle 51, which is a straight needle, and a thread 52 connected to the base portion of the straight needle. The thread 52 is used in the automatic needle mover 1 in a state of being, for example, held by the operator of the automatic needle mover 1. In the automatic needle mover 1, the operation of delivering the straight needle 51 of the threaded needle 50 from the second needle support portion 22 toward the first needle support portion 21 is performed.

As illustrated in FIGS. 3 and 4, the first needle support portion 21 and the second needle support portion 22 have a first claw portion 23 and a second claw portion 24, which protrude in the Z-axis positive direction from the first shaft 11 and the second shaft 12, respectively. The lengths of protrusion of the first claw portion 23 and the second claw portion 24 (lengths along the Z-axis direction) are, for example, approximately 3 mm to 4 mm. In addition, the lengths of the first claw portion 23 and the second claw portion 24 (thicknesses in the longitudinal direction of the first shaft 11 and the second shaft 12: lengths along the X-axis direction) are, for example, approximately 1 mm to 2 mm. In addition, the materials of the first claw portion 23 and the second claw portion 24 may be the same as or different from the materials of the first shaft 11 and the second shaft 12.

In addition, the first claw portion 23 of the first needle support portion 21 is provided with a first groove portion 25 extending in the sliding direction (longitudinal direction of the first shaft 11: X-axis direction). The width of the first groove portion 25 is smaller than the diameter of the straight needle 51. However, the width of the first groove portion 25 is a width at which the straight needle 51 can be inserted by the elasticity of the first claw portion 23 and the straight needle 51 can be held in the first groove portion 25 by the friction between the first groove portion 25 and the straight needle 51 when the straight needle 51 is inserted along the direction of extension of the first groove portion 25 (longitudinal direction of the first shaft 11: X-axis direction). For example, the width of the first groove portion 25 can be approximately 0.1 mm to 0.3 mm in a case where the outer diameter of the straight needle 51 of the threaded needle 50 is 0.4 mm and the material of the first claw portion 23 is stainless steel.

As illustrated in FIG. 4, the first groove portion 25 has a narrow portion 26 with the smallest width in the middle thereof when viewed along the direction of extension of the first groove portion 25 (longitudinal direction of the first shaft 11: X-axis direction). In addition, the width of the first groove portion 25 is tapered so as to gradually decrease from both end portions thereof toward the narrow portion 26. As a result, the straight needle 51 receives the greatest friction in the narrow portion 26 and is supported by the first groove portion 25 when the straight needle 51 is inserted in the first groove portion 25. In addition, the tapered part has a function of regulating the direction of movement of the straight needle 51 inserted in the first groove portion 25 and guiding the straight needle 51 toward the narrow portion 26.

Although the taper angle of the part of the first groove portion 25 that is tapered toward the narrow portion 26 is not particularly limited, the angle can be, for example, approximately 2° to 45° with respect to the direction of extension of the first shaft 11 and the second shaft 12. The taper angle of the tapered part thereof that is on the side closer to the second needle support portion 22 than the narrow portion 26 can be, for example, approximately 10° to 45° with respect to the direction of extension of the first shaft 11 and the second shaft 12. By the taper angles of the parts being set to the above ranges, the straight needle 51 can be suitably guided to the narrow portion 26 and the straight needle 51 can be suitably supported by the narrow portion 26. In addition, the taper angle of the tapered part that is on the side fir from the second needle support portion 22 can be, for example, approximately 2° to 10°, preferably 2° to 5°, and more preferably 2° to 3° with respect to the direction of extension of the first shaft 11 and the second shaft 12. By the taper angle of the tapered part on the side farther from the second needle support portion 22 than the narrow portion 26 being set to the above range, the straight needle 51 can be suitably supported by the narrow portion 26.

In addition, the second claw portion 24 of the second needle support portion 22 is provided with a second groove portion 27 extending in the sliding direction (longitudinal direction of the second shaft 12: X-axis direction). The second groove portion 27 has a first region 28 provided on the first needle support portion 21 side and having a width larger than the diameter of the straight needle 51 and a second region 29 provided on the handle 30 side and having a width smaller than the diameter of the straight needle 51 and larger than the diameter of the thread 52. Accordingly, when the thread 52 of the threaded needle 50 is inserted into the second groove portion 27 and the thread 52 is pulled to the handle 30 side with the straight needle 51 disposed on the first needle support portion 21 side, the straight needle 51 is supported in the second groove portion 27 by the straight needle 51 of the threaded needle 50 being caught in the second region 29 of the second groove portion 27. The width of the first region 28 of the second groove portion 27 can be approximately 0.41 mm to 0.42 mm and the width of the second region 29 can be approximately 0.2 mm to 0.3 mm in a case where, for example, the outer diameter of the straight needle 51 of the threaded needle 50 is 0.4 mm, the outer diameter of the thread 52 is 0.15 mm, and the material of the second claw portion 24 is stainless steel. The length of the second region 29 (thickness in the longitudinal direction of the second shaft 12: length along the X-axis direction) is not particularly limited insofar as the straight needle 51 can be supported in the second region 29.

As illustrated in FIG. 4, both the second needle support portion 22 side end surface of the first claw portion 23 constituting the first needle support portion 21 and the first needle support portion 21 side end surface of the second claw portion 24 constituting the second needle support portion 22 are flat surfaces parallel to each other. Accordingly, a state where the first groove portion 25 of the first needle support portion 21 and the second groove portion 27 of the second needle support portion 22 are continuous is formed in a state where the first needle support portion 21 and the second needle support portion 22 abut against each other.

In the automatic needle mover 1 described above, the second needle support portion 22 functions as a needle holding portion holding the straight needle 51 that is yet to be delivered and the second claw portion 24 and the second groove portion 27 function as the first claw portion and the first groove portion in the needle holding portion. In addition, the first needle support portion 21 functions as a needle-receiving portion holding the straight needle 51 that has been delivered and the first claw portion 23 and the first groove portion 25 function as the second claw portion and the second groove portion in the needle-receiving portion.

Figure 5:
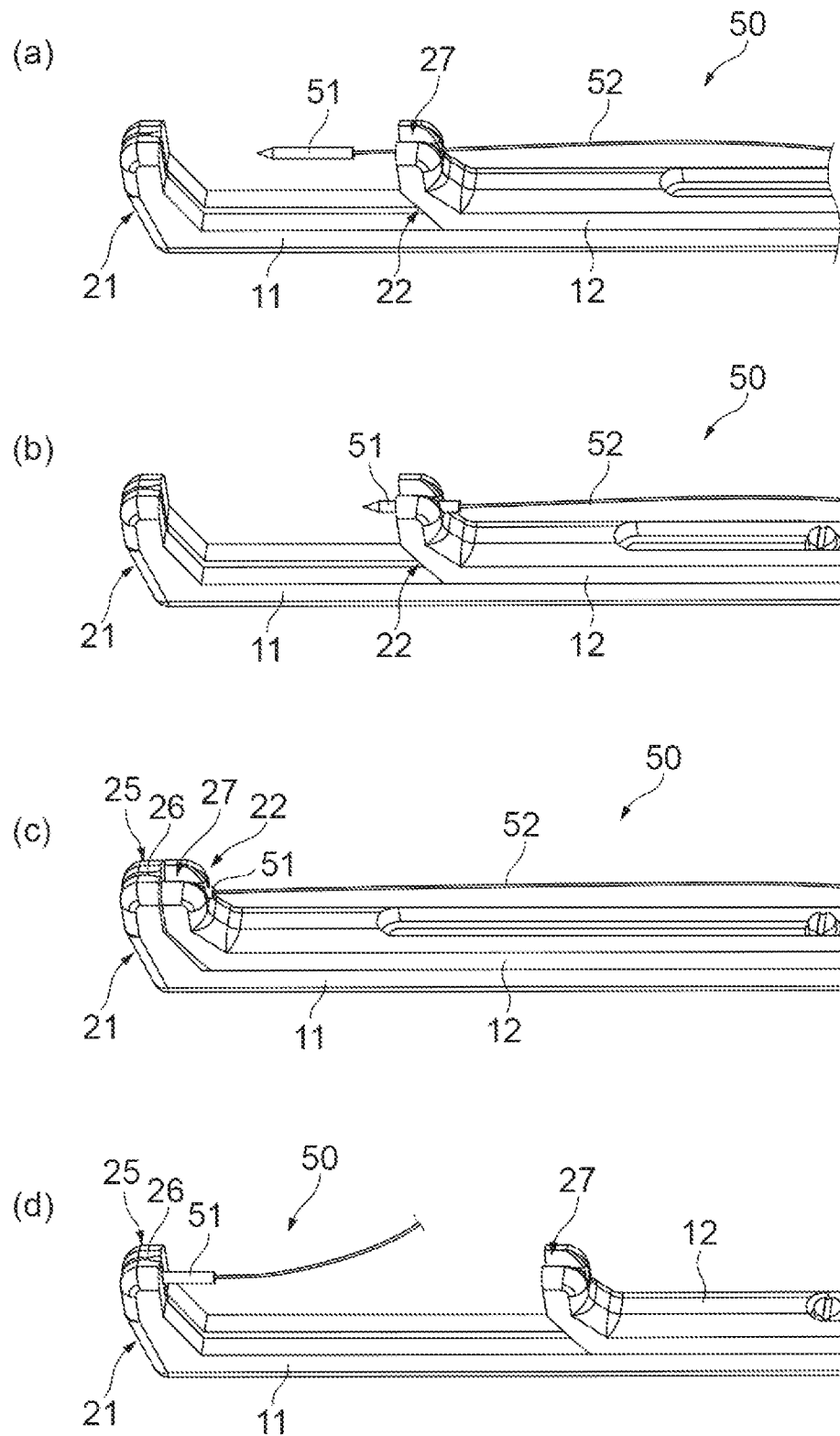
FIG. 5 is a diagram describing threaded needle delivery in the automatic needle mover.

Next, the delivery of the threaded needle 50 (straight needle 51 in particular) in the automatic needle mover 1 will be described with reference to FIG. 5.

First, as illustrated in FIG. 5(a), the first needle support portion 21 and the second needle support portion 22 are separated from each other and the second groove portion 27 of the second needle support portion 22 accommodates the thread 52 of the threaded needle 50 by the second shaft 12 being slid with respect to the first shaft 11. At this time, the straight needle 51 of the threaded needle 50 is disposed on the first needle support portion 21 side. When the operator of the automatic needle mover 1 pulls the thread 52 of the threaded needle 50 to the handle 30 side in this state, the straight needle 51 of the threaded needle 50 is caught in the second region 29 of the second groove portion 27 as illustrated in FIG. 5(b). As a result, the straight needle 51 of the threaded needle 50 is held in the second groove portion 27 of the second needle support portion 22.

Next, the second shaft 12 is slid with respect to the first shaft 11. As a result, the second needle support portion 22 abuts against the first needle support portion 21 as illustrated in FIG. 5(c). The straight needle 51 of the threaded needle 50 supported by the second needle support portion 22 also moves along with the movement of the second needle support portion 22, and the tip thereof is inserted into the first groove portion 25 of the first needle support portion 21.

Although the sliding speed of the second shaft 12 with respect to the first shaft 11 is determined by the speed of operation of the handle 30 by the operator of the automatic needle mover 1, the first needle support portion 21 and the second needle support portion 22 abut against each other with some speed. The tip of the straight needle 51 supported by the second groove portion 27 of the second needle support portion 22 is inserted into the first groove portion 25 of the first needle support portion 21 and passes through the narrow portion 26. As a result, the tip of the straight needle 51 is sandwiched by the narrow portion 26 and the straight needle 51 is held by the first groove portion 25 of the first needle support portion 21.

Subsequently, the first needle support portion 21 and the second needle support portion 22 are separated from each other by the second shaft 12 being slid with respect to the first shaft 11. At this time, the holding force of the straight needle Si by the first needle support portion 21 is larger than the holding three by the second needle support portion 22, and thus the straight needle 51 is held by the first needle support portion 21. In other words, the straight needle 51 is delivered from the second needle support portion 22 to the first needle support portion 21.

In the serial operations described above, the tissue to be sutured or the like can be penetrated by the straight needle Si by the tip part of the automatic needle mover 1 being disposed such that the tissue to be sutured is disposed between the first needle support portion 21 and the second needle support portion 22 and the straight needle 51 being delivered from the second needle support portion 22 to the first needle support portion 21 as illustrated in FIGS. 5(c) to 5(d). After the tissue to be sutured is penetrated by the straight needle 51, the automatic needle mover 1 is moved such that, for example, no tissue is disposed between the first needle support portion 21 and the second needle support portion 22, and then the automatic needle mover 1 is pulled back to the operator side. As a result, the thread 52 in the latter stage of the straight needle 51 passes through the through hole formed in the tissue by the straight needle 51.

As described above, in the automatic needle mover 1 according to the present embodiment, the first needle support portion 21 functioning as the needle-receiving portion is provided in the end portion of the first shaft 11 and the second needle support portion 22 functioning as the needle holding portion is provided in the end portion of the second shaft 12 extending in the same direction as the first shaft 11. Further, as for the first shaft 11 and the second shaft 12, the second shaft 12 slides along the longitudinal direction with respect to the first shaft 11 as a result of the operation of the handle 30. As a result of this operation, the straight needle 51 can be delivered from the needle holding portion of the second needle support portion 22 to the needle-receiving portion of the first needle support portion 21. Accordingly, in the automatic needle mover 1, the medical threaded needle can be moved on a suture surface that intersects the longitudinal direction of the instrument (direction of extension of the first shaft 11 and the second shaft 12).

Although a needle mover has been used for suturing tissue deep inside the body or the like in the related art, it has been difficult to move a needle along the longitudinal direction of the instrument with the needle mover of the related art. Accordingly, it has been difficult to perform suturing in a place where a sufficient space for suturing work cannot be secured. In a case where suturing work is performed deep inside the body after insertion from a body surface opening, examples of which include a case where the deep brain is approached from the nasal cavity, the space where the instrument for approaching the deep part in the body is movable is limited and the space for performing the suturing work deep inside the body is also narrow. Further, suturing work by means of the needle mover according to the related art has been difficult in many cases in a case where the direction of the suture surface intersects the longitudinal direction of the instrument.

On the other hand, the automatic needle mover 1 according to the present embodiment has a configuration in which the straight needle 51 can be delivered from the needle holding portion of the second needle support portion 22 to the needle-receiving portion of the first needle support portion 21, and thus the needle can be moved along the longitudinal direction of the instrument. Accordingly, the needle movement for suturing can be suitably performed even in a case where the space in the direction intersecting the longitudinal direction of the instrument is narrow and the movement of the instrument is restricted in particular.

In addition, in the automatic needle mover 1, the first needle support portion 21 functioning as the needle-receiving portion is farther from the handle 30 than the second needle support portion 22 functioning as the needle holding portion along the longitudinal direction of the first shaft 11 and the second shaft 12. Accordingly the straight needle can be moved in the direction away from the handle 30 as a result of the straight needle delivery from the needle holding portion to the needle-receiving portion.

In addition, in the automatic needle mover 1, the first groove portion 25 of the first needle support portion 21 has the narrow portion 26 in the middle thereof when viewed along the direction of extension of the first groove portion 25 (longitudinal direction of the first shaft 11: X-axis direction) and has a structure in which the straight needle 51 inserted in the first groove portion 25 receives the greatest friction in the narrow portion 26 and is supported by the first groove portion 25. By having such a structure, the straight needle 51 supported in the first groove portion 25 of the first needle support portion 21 is capable of pivoting along the surface where the first groove portion 25 is formed about the narrow portion 26 while maintaining the state of being supported by the first needle support portion 21. Accordingly, the straight needle 51 is capable of pivoting about the narrow portion 26 in the first groove portion of the first needle support portion 21 when, for example, the automatic needle mover 1 is moved such that no tissue is disposed between the first needle support portion 21 and the second needle support portion 22. Accordingly, the automatic needle mover 1 can be moved (in, for example, the Z-axis negative direction in FIG. 3) such that no tissue is disposed between the first needle support portion 21 and the second needle support portion 22 without the straight needle 51 being moved in the direction away from the handle 30 (X-axis negative direction) along the direction of extension of the first groove portion 25 (longitudinal direction of the first shaft 11: X-axis direction). Since the first groove portion 25 has the narrow portion 26 as described above, the straight needle 51 can be suitably moved even in a case where a space for performing suturing work is narrower.

It should be noted that the first needle support portion 21 and the second needle support portion 22 do not have to abut against each other although a case where the first needle support portion 21 and the second needle support portion 22 "abut against each other" has been described in the embodiment and it suffices if the first needle support portion 21 and the second needle support portion 22 are capable of becoming close to each other to the extent that the straight needle 51 can be delivered between the first needle support portion 21 and the second needle support portion 22 by sliding between the first shaft 11 and the second shaft 12. It suffices if the needle holding portion (second needle support portion 22) and the needle-receiving portion (first needle support portion 21) are capable of becoming close to each other and the straight needle 51 held by the needle holding portion (second needle support portion 22) can be press-fitted into the needle-receiving portion (first needle support portion 21) as a result of the sliding of the two shafts, that is, the first shaft 11 and the second shaft 12. Accordingly, when the straight needle 51 is delivered, a gap of, for example, approximately 1 mm to several millimeters may be provided without the first needle support portion 21 and the second needle support portion 22 abutting against each other. This point also applies to the automatic needle movers to be described in the following embodiments.

Second Embodiment

Figure 6:
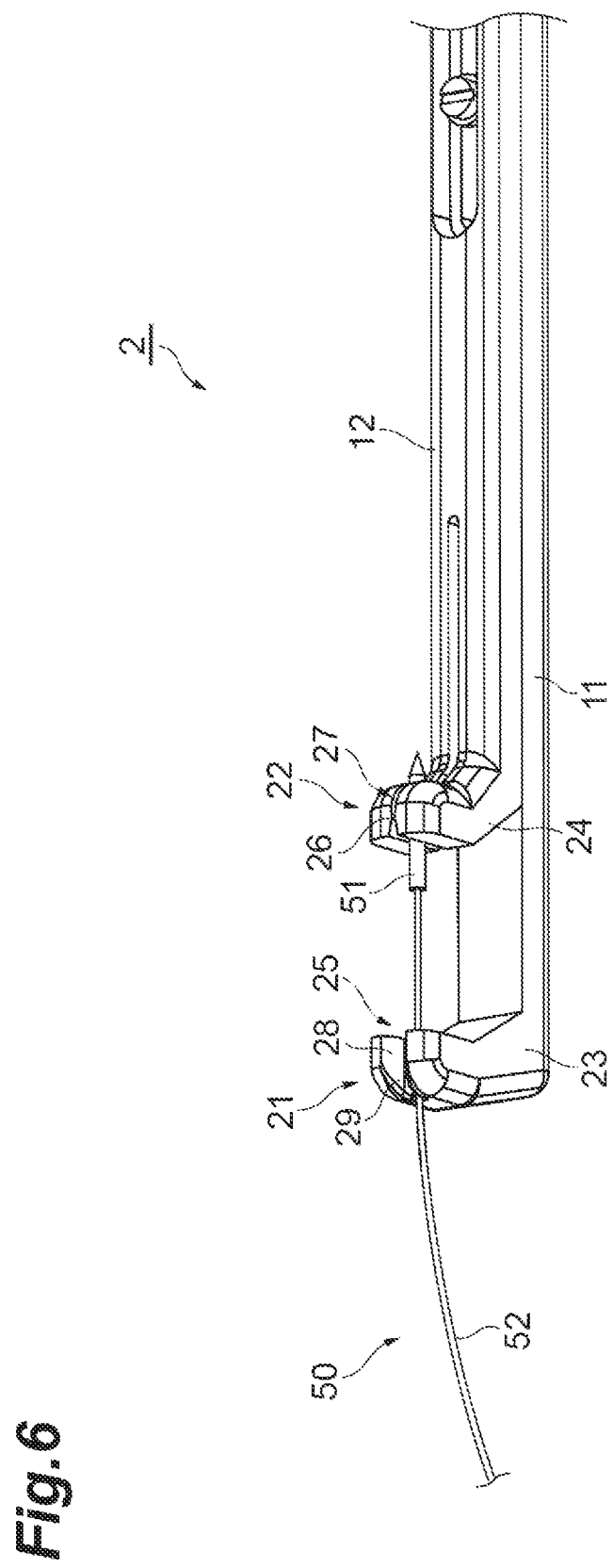
FIG. 6 is a perspective view of the tip part of the automatic needle mover according to a second embodiment.
Figure 7:
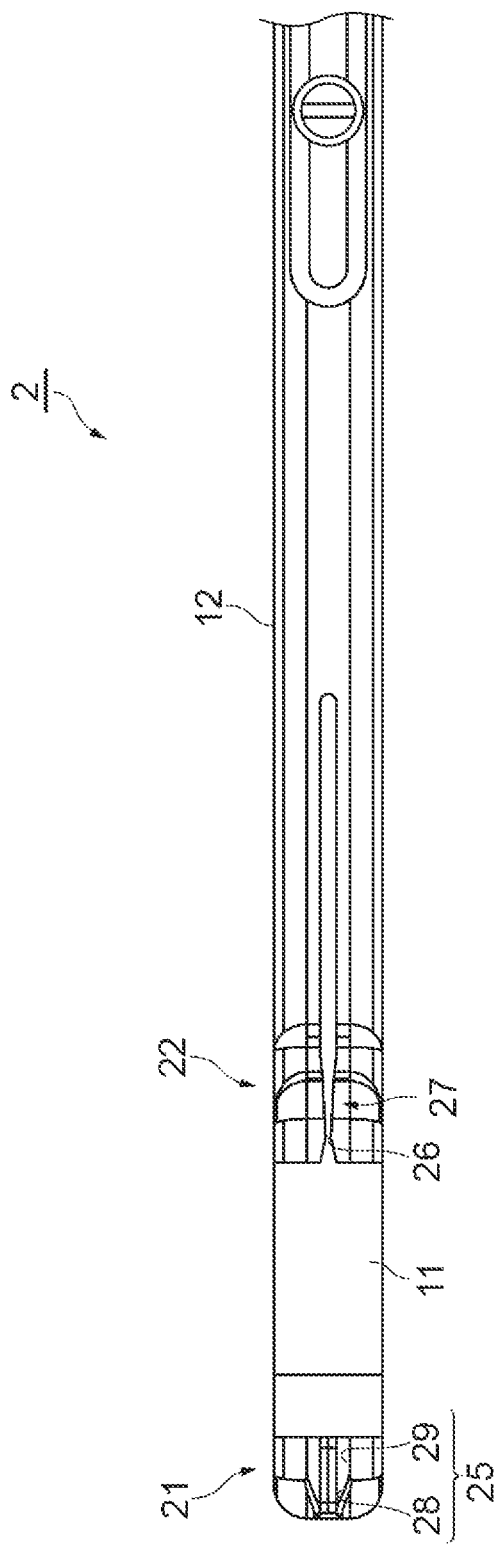
FIG. 7 is a plan view of the tip part of the automatic needle mover.

Next, a second embodiment of the automatic needle mover will be described with reference to FIGS. 6 and 7. FIG. 6 is a perspective view of the tip part of an automatic needle mover 2 according to the second embodiment, and FIG. 7 is a plan view of the tip part.

The automatic needle mover 2 illustrated in FIGS. 6 and 7 differs from the automatic needle mover 1 in the following points. In other words, in the automatic needle mover 2, the first needle support portion 21 functions as the needle holding portion holding the straight needle 51 that is yet to be delivered and the second needle support portion 22 functions as the needle-receiving portion holding the straight needle 51 that has been delivered. Accordingly, in the automatic needle mover 2, the functions of the first needle support portion 21 and the second needle support portion 22 are opposite to those in the automatic needle mover 1.

The first needle support portion 21 and the second needle support portion 22 of the automatic needle mover 2 are provided with the first claw portion 23 and the second claw portion 24, which protrude in a direction intersecting the longitudinal direction of the first shaft 11 and the second shaft 12, respectively.

The first claw portion 23 of the first needle support portion 21 is provided with the first groove portion 25 extending in the sliding direction (longitudinal direction of the first shaft 11: X-axis direction). However, as in the case of the second groove portion 27 of the automatic needle mover 1, the first groove portion 25 of the automatic needle mover 2 has the first region 28 provided on the second needle support portion 22 side and having a width larger than the diameter of the straight needle 51 and the second region 29 provided on the tip side of the automatic needle mover 2 and having a width smaller than the diameter of the straight needle 51 and larger than the diameter of the thread 52 (see FIG. 7), Accordingly, the straight needle 51 can be held with respect to the first groove portion 25 by means of the first region 28 of the first needle support portion 21.

In addition, the second claw portion 24 of the second needle support portion 22 is provided with the second groove portion 27 extending in the sliding direction (longitudinal direction of the second shaft 12: X-axis direction). The width of the second groove portion 27 is smaller than the diameter of the straight needle 51. However, the width of the second groove portion 27 is a width at which the straight needle 51 can be inserted by the elasticity of the second claw portion 24 and the straight needle 51 can be held in the second groove portion 27 by the friction between the second groove portion 27 and the straight needle 51 when the straight needle 51 is inserted from the first needle support portion 21 side along the direction of extension of the second groove portion 27 (longitudinal direction of the second shaft 12: X-axis direction). In addition, the narrow portion 26 is also provided in the second groove portion 27.

Also in the automatic needle mover 2 having the above structure, the medical threaded needle can be moved on a suture surface that intersects the longitudinal direction of the instrument (direction of extension of the first shaft 11 and the second shaft 12). However, the direction of movement of the needle is opposite to that in the automatic needle mover 1. Although the procedure of needle movement by means of the automatic needle mover 2 is substantially the same as that by means of the automatic needle mover the disposition of the needle holding portion and the needle-receiving portion is opposite, and thus the needle movement direction is reversed.

Specifically, the procedure is as follows. First, the first needle support portion 21 and the second needle support portion 22 are separated from each other and the first groove portion 25 of the first needle support portion 21 accommodates the thread 52 of the threaded needle 50 by the second shaft 12 being slid with respect to the first shaft 11. At this time, the straight needle 51 of the threaded needle 50 is disposed on the second needle support portion 22 side. When the operator of the automatic needle mover 1 pulls the thread 52 of the threaded needle 50 to the tip side of the automatic needle mover 2 (side opposite to the handle 30 side) in this state, the straight needle 51 of the threaded needle 50 is caught in the second region 29 of the second groove portion 27. As a result, the straight needle 51 of the threaded needle 50 is held in the second groove portion 27 of the first needle support portion 21.

Next, the second shaft 12 is slid with respect to the first shaft 11. As a result, the second needle support portion 22 abuts against the first needle support portion 21. When the second needle support portion 22 abuts against the first needle support portion 21, the tip of the straight needle 51 is inserted into the second groove portion 27 of the second needle support portion 22 and passes through the narrow portion 26. As a result, the tip of the straight needle 51 is sandwiched by the narrow portion 26 and the straight needle 51 is held by the second groove portion 27 of the second needle support portion 22.

Subsequently, the first needle support portion 21 and the second needle support portion 22 are separated from each other by the second shaft 12 being slid with respect to the first shaft 11. At this time, the holding force of the straight needle 51 by the second needle support portion 22 is larger than the holding force by the first needle support portion 21, and thus the straight needle 51 is held by the second needle support portion 22. In other words, the straight needle 51 is delivered from the first needle support portion 21 to the second needle support portion 22. FIG. 6 illustrates a state where the straight needle 51 of the threaded needle 50 is delivered from the first needle support portion 21 to the second needle support portion 22.

In the serial operations described above, the tissue to be sutured or the like can be penetrated by the straight needle 51 by the tip part of the automatic needle mover 2 being disposed such that the tissue to be sutured is disposed between the first needle support portion 21 and the second needle support portion 22 and the straight needle 51 being delivered from the first needle support portion 21 to the second needle support portion 22. After the tissue to be sutured is penetrated by the straight needle 51, the automatic needle mover 1 is moved such that, for example, no tissue is disposed between the first needle support portion 21 and the second needle support portion 22, and then the automatic needle mover 1 is pulled back to the operator side. As a result, the thread 52 in the latter stage of the straight needle 51 passes through the through hole formed in the tissue by the straight needle 51.

As described above, in the automatic needle mover 2, the first needle support portion 21 functioning as the needle holding portion is provided in the end portion of the first shaft 11 and the second needle support portion 22 functioning as the needle-receiving portion is provided in the end portion of the second shaft 12 extending in the same direction as the first shaft 11. Further, as for the first shaft 11 and the second shaft 12, the second shaft 12 slides along the longitudinal direction with respect to the first shaft 11 as a result of the operation of the handle 30. As a result of this operation, the straight needle 51 can be delivered from the needle holding portion of the first needle support portion 21 to the needle-receiving portion of the second needle support portion 22. Accordingly, also in the automatic needle mover 2, the medical threaded needle can be moved on a suture surface that intersects the longitudinal direction of the instrument (direction of extension of the first shaft 11 and the second shaft 12).

In addition, the needle movement directions of the straight needle 51 are opposite to each other in the automatic needle mover 1 and the automatic needle mover 2. In the automatic needle mover 1, the straight needle 51 can be moved from the handle 30 side toward the tip of the automatic needle mover 1 (side where the first needle support portion 21 and the second needle support portion 22 are provided), that is, in a direction away from the handle 30 (X-axis negative direction). On the other hand, in the automatic needle mover 2, the straight needle 51 can be moved from the tip of the automatic needle mover 1 (side where the first needle support portion 21 and the second needle support portion 22 are provided) to the handle 30 side, that is, in a direction toward the handle 30 (X-axis positive direction).

Accordingly, by the automatic needle mover 1 and the automatic needle mover 2 being used in combination, the medical threaded needle can be moved in both the direction away from the operator and the direction toward the operator on a suture surface intersecting the longitudinal direction of the instrument (direction of extension of the first shaft 11 and the second shaft 12) and the suture surface can be suitably sutured. It should be noted that a specific procedure for suturing the tissue with the automatic needle mover 1 and the automatic needle mover 2 is as follows. For example, in a case where it is desired to perform suturing between two deep body tissue points, the threaded needle 50 is set first ire the automatic needle mover 1 outside the body, the threaded needle 50 is inserted into the body; one point of the tissue is penetrated by the straight needle 51, and then the straight needle 51 is pulled out of the body as it is. Next, the threaded needle 50 is removed from the automatic needle mover 1 outside the body, reset in the automatic needle mover 2, and reinserted into the body while the slack of the thread 52 is removed and the other point in the tissue to be sutured is penetrated by the needle. Finally, the threaded needle 50 is pulled out of the body together with the automatic needle mover 2, a knot is tied, and then ligation is performed by the knot being sent into the body by means of a knot pusher or the like and the suturing is completed. By the automatic needle mover 1 and the automatic needle mover 2 being used in combination as described above, suturing on a suture surface intersecting the longitudinal direction of the instrument (direction of extension of the first shaft 11 and the second shaft 12) can be suitably performed.

Third Embodiment

Figure 8:
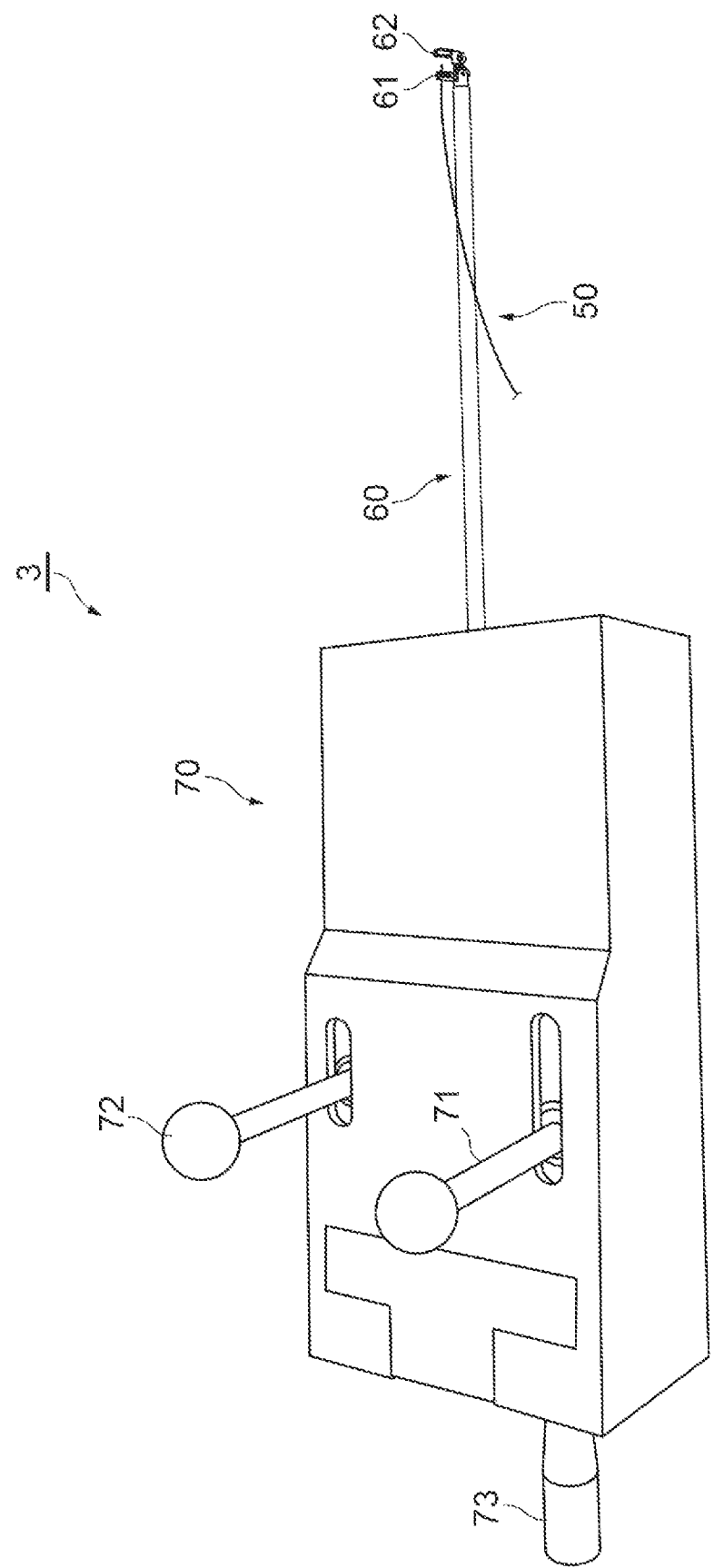
FIG. 8 is a perspective view of the automatic needle mover according to a third embodiment.
Figure 9:
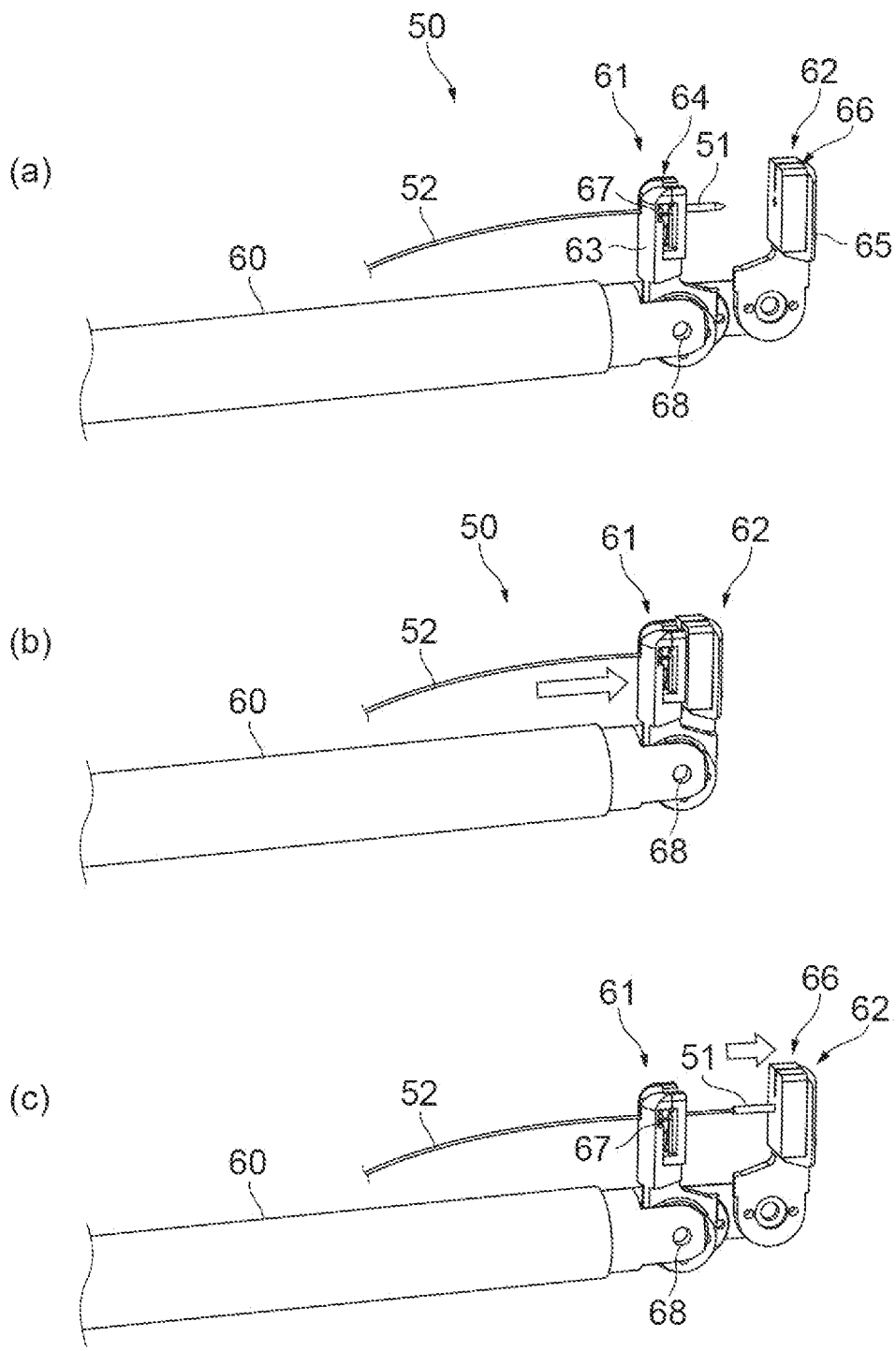
FIG. 9 is a diagram describing threaded needle delivery in the automatic needle mover.

Next, a third embodiment of the automatic needle mover will be described with reference to FIGS. 8 to 10. FIG. 8 is a schematic configuration diagram of an automatic needle mover 3 according to the third embodiment, and FIGS. 9 and 10 are perspective views of the tip part of the automatic needle mover 3 for describing how to use the automatic needle mover 3.

The automatic needle mover 3 described as the third embodiment has functions as the automatic needle mover 1 and the automatic needle mover 2. In other words, with the automatic needle mover 3, the medical threaded needle can be moved in both the direction away from the operator and the direction toward the operator on a suture surface intersecting the longitudinal direction of the instrument (direction of extension of the first shaft 11 and the second shaft 12). Accordingly, the automatic needle mover 3 has a shaft portion 60 extending in the longitudinal direction as in the case of the first shaft 11 and the second shaft 12 in the automatic needle mover 1, a needle holding portion 61 provided in the tip portion of the shaft portion 60 and having the same function as the needle holding portion in the automatic needle mover 1 (second needle support portion 22 of the second shaft 12), a needle-receiving portion 62 provided in the tip portion of the shaft portion 60 and having the same function as the needle-receiving portion in the automatic needle mover 1 (first needle support portion 21 of the first shaft 11), and a control unit 70 controlling the operation of the needle holding portion 61 and the needle-receiving portion 62.

The shaft portion 60 integrally constitutes the first shaft 11 and the second shaft 12 and has the same function as the first shaft 11 and the second shaft 12. In other words, the shaft portion 60 has a function for changing the positional relationship between the needle holding portion 61 and the needle-receiving portion 62. In addition, the shaft portion 60 has a function of transmitting, to each portion, the control that is performed by the control unit 70 and related to the pivoting of the needle holding portion 61 and the needle-receiving portion 62 (described later) and control operation such as the operation of a hook 67 in the needle holding portion 61.

The needle holding portion 61 has a claw portion 63 and a groove portion 64 formed in the claw portion 63 as in the case of the needle holding portion in the automatic needle mover 1 and the automatic needle mover 2. The groove portion 64 has a first region provided on the second needle support portion 22 side (side facing the needle-receiving portion) and having a width larger than the diameter of the straight needle 51 and a second region provided on the handle 30 side (side away from the needle-receiving portion) and having a width smaller than the diameter of the straight needle 51 and larger than the diameter of the thread 52. Accordingly, the holding capacity of the straight needle 51 in the needle holding portion 61 is substantially the same as that of the needle holding portion in the automatic needle mover 1 and the automatic needle mover 2. Further, the needle holding portion 61 has the hook 67 physically holding the straight needle 51 in a case where the needle holding portion 61 holds the straight needle 51. The straight needle 51 is delivered from the needle-receiving portion 62 to the needle holding portion 61 by means of the hook 67. Details will be described later.

The needle-receiving portion 62 has a claw portion 65 and a groove portion 66 formed in the claw portion 65 as in the case of the needle-receiving portion in the automatic needle mover 1 and the automatic needle mover 2. The groove portion 66 extends in the direction of movement of the shaft portion 60. The width of the groove portion 66 is smaller than the diameter of the straight needle 51. However, the width of the groove portion 66 is a width at which the straight needle 51 can be inserted by the elasticity of the claw portion 63 and the straight needle 51 can be held in the groove portion 66 by the friction between the groove portion 66 and the straight needle 51 when the straight needle 51 is inserted from the needle holding portion 61 side along the direction of extension of the groove portion 66.

The needle holding portion 61 and the needle-receiving portion 62 are pivotable about a pivot shaft 68 provided at the tip of the shaft portion 60. The pivot shaft 68 extends in a direction intersecting the direction of extension of the shaft portion 60 (direction orthogonal to the direction of extension of the shaft portion 60 in the example illustrated in FIGS. 9 and 10). In addition, the needle-receiving portion 62 is slidable along the direction of extension of the shaft portion 60 with respect to the needle holding portion 61. Accordingly, the distance between the needle holding portion 61 and the needle-receiving portion 62 can be changed and the needle holding portion 61 and the needle-receiving portion 62 are capable of abutting against each other and can be separated from each other as in the case of the automatic needle mover 1 and the automatic needle mover 2.

The control unit 70 has a function of performing, for example, the pivoting of the needle holding portion 61 and the needle-receiving portion 62 about the pivot shaft 68, the movement (sliding) of the needle-receiving portion 62 along the direction of extension of the shaft portion 60, and the control of the hook 67 in the needle holding portion 61. To that end, the control unit 70 has operation levers 71 to 73 or the like. The disposition of the operation levers 71 to 73, the functions of the operation levers 71 to 73, and so on are not particularly limited.

Next, the movement of the threaded needle 50 (straight needle 51 in particular) in the automatic needle mover 3 will be described with reference to FIGS. 9 and 10.

First, the needle holding portion 61 and the needle-receiving portion 62 are separated from each other and the thread 52 of the threaded needle 50 is accommodated in the groove portion 64 of the needle holding portion 61 as illustrated in FIG. 9(a). At this time, the tip of the straight needle 51 of the threaded needle 50 is disposed on the needle-receiving portion 62 side. When the operator of the automatic needle mover 3 pulls the thread 52 of the threaded needle 50 to the handle 30 side in this state, the straight needle 51 of the threaded needle 50 is caught in the second region of the second groove portion 27 as illustrated in HG 9(a). As a result, the straight needle 51 of the threaded needle 50 is held in the groove portion 64 of the needle holding portion 61.

Next, the needle holding portion 61 abuts against the needle-receiving portion 62 under the control of the control unit 70 as illustrated in FIG. 9(h). The straight needle 51 of the threaded needle 50 supported by the needle holding portion 61 also moves along with the movement of the needle holding portion 61, and the tip thereof is inserted into the groove portion 66 of the needle-receiving portion 62.

Subsequently, the needle-receiving portion 62 and the needle holding portion 61 are separated from each other. At this time, the holding force of the straight needle 51 by the needle-receiving portion 62 is larger than the holding force by the needle holding portion 61, and thus the straight needle 51 is held by the needle-receiving portion 62. In other words, the straight needle 51 is delivered from the needle holding portion 61 to the needle-receiving portion 62 as illustrated in FIG. 9(c).

In the serial operations described above, the tissue to be sutured or the like can be penetrated by the straight needle 51 by the tip part of the automatic needle mover 3 being disposed such that the tissue to be sutured is disposed between the needle holding portion 61 and the needle-receiving portion 62 and the straight needle 51 being delivered from the needle holding portion 61 to the needle-receiving portion 62.

After the tissue to be sutured is penetrated by the straight needle 51, the automatic needle mover 1 is moved such that, for example, no tissue is disposed between the needle holding portion 61 and the needle-receiving portion 62, and then the straight needle 51 is pulled back from the needle-receiving portion 62 to the needle holding portion 61 side. Specifically, the needle holding portion 61 is caused to re-abut against the needle-receiving portion 62 in a place away from the tissue to be sutured or the like. At this time, the thread 52 side end portion of the straight needle 51 held on the needle-receiving portion 62 side is accommodated in the groove portion 64 of the needle holding portion 61. Here, the straight needle 51 is fixed in the groove portion 64 of the needle holding portion 61 by means of the hook 67 and the needle-receiving portion 62 and the needle holding portion 61 are separated from each other in that state. Then, the straight needle 51 moves to the needle holding portion 61 side again. This delivery of the straight needle 51 to the needle holding portion 61 side can be performed in a state where the tip part of the automatic needle mover 3 is pulled back to the operator side from the vicinity of the tissue to be sutured.

Next, the needle is moved such that the straight needle 51 faces the operator side on the suture surface. First, as illustrated in FIGS. 10(a) and 10(b), the needle holding portion 61 and the needle-receiving portion 62 are separated from each other and the needle holding portion 61 and the needle-receiving portion 62 are pivoted by approximately 180 degrees about the pivot shaft 68 as an axis. As a result, the needle holding portion 61 is disposed on the far side (side away from the operator) with respect to the needle-receiving portion 62 after the pivoting (state illustrated in FIG. 10(b)) whereas the needle holding portion 61 is provided on the operator side with respect to the needle-receiving portion 62 before the pivoting (state illustrated in FIGS. 9(a) to 9(c)). In other words, the positional relationship between the needle holding portion 61 and the needle-receiving portion 62 along the longitudinal direction of the shaft portion 60 is reversed. In addition, the straight needle 51 pivots while being held by the needle holding portion 61 and thus the tip of the straight needle 51 after the pivoting is disposed so as to face the operator side.

In the state that is illustrated in FIG. 10(b), the needle holding portion 61 and the needle-receiving portion 62 are separate from each other by the needle-receiving portion 62 being slid along the shaft portion 60. In this state, the needle holding portion 61 abuts against the needle-receiving portion 62 as illustrated in FIG. 10(c) under the control of the control unit 70. Then, the straight needle 51 of the threaded needle 50 supported by the needle holding portion 61 also moves along with the movement of the needle holding portion 61 and the tip thereof is inserted into the groove portion 66 of the needle-receiving portion 62.

Subsequently, the needle-receiving portion 62 and the needle holding portion 61 are separated from each other. At this time, the holding force of the straight needle 51 by the needle-receiving portion 62 is larger than the holding force by the needle holding portion 61, and thus the straight needle 51 is held by the needle-receiving portion 62. In other words, the straight needle 51 is delivered from the needle holding portion 61 to the needle-receiving portion 62 as illustrated in FIG. 10(d).

In the serial operations subsequent to the pivoting of the needle holding portion 61 and the needle-receiving portion 62 along the pivot shaft 68, the tissue to be sutured or the like can be penetrated by the straight needle 51 by the tip part of the automatic needle mover 3 being disposed such that the tissue to be sutured is disposed between the needle holding portion 61 and the needle-receiving portion 62 and the straight needle 51 being delivered from the needle holding portion 61 to the needle-receiving portion 62. The direction of penetration by the straight needle 51 at this time is from the far side of the operator toward the side close to the operator, that is, toward the operator.

After the tissue to be sutured is penetrated by the straight needle 51, the automatic needle mover 3 is moved such that, for example, no tissue is disposed between the needle holding portion 61 and the needle-receiving portion 62, and then the tip of the automatic needle mover 3 is pulled back to the operator side. As a result, suturing by means of the automatic needle mover 3 is performed. In particular, the straight needle 51 is moved in both the direction away from the operator and the direction toward the operator.

As described above, also in the automatic needle mover 3 according to the third embodiment, the medical threaded needle can be moved in both the direction away from the operator and the direction toward the operator on a suture surface intersecting the longitudinal direction of the instrument (direction of extension of the shaft portion 60) and the suture surface can be suitably sutured. In addition, the straight needle 51 can be moved in both the direction away from the operator and the direction toward the operator in the automatic needle mover 3, and thus there is no need to switch and use a needle mover capable of moving the straight needle 51 in a specific direction, such as the automatic needle mover 1 and the automatic needle mover 2, and work efficiency is improved.

Fourth Embodiment

Figure 11:
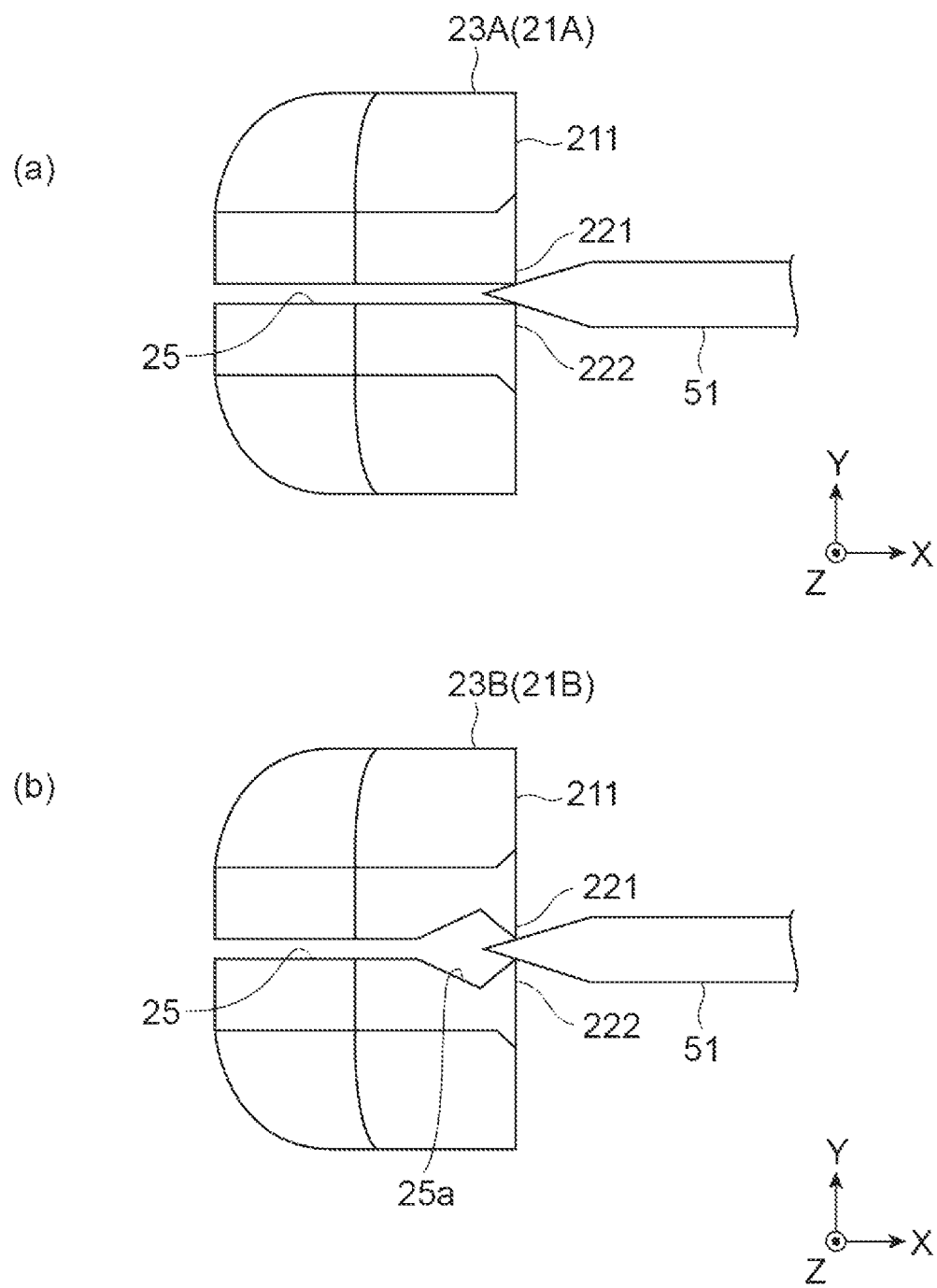
FIG. 11 is a diagram describing the needle-receiving portion of the automatic needle mover according to a fifth embodiment.

Next, a fourth embodiment of the automatic needle mover will be described with reference to FIG. 11. Described in the fourth embodiment is an example in which the shape of the first needle support portion 21 functioning as the needle-receiving portion holding the straight needle 51 that has been delivered in the automatic needle mover 1 described in the first embodiment is changed. FIGS. 11(a) and 11(b) are diagrams illustrating modification examples of the first needle support portion 21 and are plan views of the tip part of the first needle support portion.

Described in the first embodiment is a case where the first groove portion 25 provided in the first claw portion 23 of the first needle support portion 21 has the narrow portion 26 with the smallest width in the middle thereof when viewed along the direction of extension of the first groove portion 25 (longitudinal direction of the first shaft 11: X-axis direction). In addition, in the first embodiment, the width of the first groove portion 25 is tapered so as to gradually decrease from both end portions thereof toward the narrow portion 26. On the other hand, the shape is different in a first needle support portion 21A illustrated in FIG. 11(a).

Specifically, in a first claw portion 23A of the first needle support portion 21A, the width of the first groove portion 25 is the same along the direction of extension of the first groove portion 25 (longitudinal direction of the first shaft 11: X-axis direction). In other words, the first groove portion 25 has a uniform thickness along the direction of extension. It should be noted that the width of the first groove portion 25 is a width at which the straight needle 51 can be held in the first groove portion 25 by the friction between the first groove portion 25 and the straight needle 51. For example, the width of the first groove portion 25 can be approximately 0.1 mm to 0.2 mm in a case where the outer diameter of the straight needle 51 of the threaded needle 50 is 0.4 mm and the material of the first claw portion 23A is stainless steel.

In addition, the end surface of the first needle support portion 21A that faces the second needle support portion, that is, an end surface 211 on the side where the straight needle 51 is inserted is a flat surface orthogonal to the direction of extension (X-axis direction) of the first groove portion 25 (that is, extending along the YZ plane). As a result, in the first needle support portion 21A, a pair of corner portions 221 and 222 having an end portion angle of 90° in a plan view are formed by the first groove portion 25 and the end surface 211 in the end surface 211 side end portion of the first groove portion 25.

When the straight needle 51 is inserted into the first groove portion 25 provided in the first claw portion 23A of the first needle support portion 21A, the straight needle 51 is inserted into the first groove portion 25 in a state of abutting against the corner portions 221 and 222 and being sandwiched between the corner portions 221 and 222. At this time, the corner portions 221 and 222 abutting against the straight needle 51 form an angle of 90° in the plan view. As a result, the tip of the straight needle 51, which is generally conical, comes into point contact with the corner portions 221 and 222 in the plan view. Although the straight needle 51 needs to penetrate the tissue to be sutured when the straight needle 51 is delivered from the second needle support portion (needle holding portion) to the first needle support portion 21A (needle-receiving portion), the tissue is fixed at the points of contact between the corner portions 221 and 222 and the straight needle 51. At this time, the tissue fixed at the points of contact between the corner portions 221 and 222 and the straight needle 51 receives a force in the direction away from the straight needle 51. In other words, the tissue is prevented from moving by following the movement of the straight needle 51 and entering, for example, the first groove portion 25 when the tip part of the straight needle 51 is inserted in the first groove portion 25.

In a case where the corner portions 221 and 222 abutting against the straight needle 51 in the end portion (end portion on the side where the straight needle 51 is inserted) of the first groove portion 25 of the first needle support portion 21A (first claw portion 23A) have an angle of 90° or an acute angle of less than 90° in a plan view as described above, the tissue is fixed at the part of abutting against the straight needle 51, and thus a movement thereof (movement toward the inside of the first groove portion 25 that follows the straight needle 51 in particular) can be regulated. Accordingly, the tissue can be prevented from, for example, entering the first groove portion 25. It is conceivable that this effect is particularly effective when a certain degree of force is required for the penetration by the straight needle 51, examples of which include a case where the tissue is dura mater. However, by the above configuration being adopted regardless of the hardness of the tissue to be penetrated, the tissue can be prevented from entering the first groove portion 25 of the first needle support portion 21A when the straight needle 51 is delivered (that is, when the tissue is penetrated by the straight needle 51).

It should be noted that the width of the first groove portion 25 being uniform along the direction of extension thereof and the end surface 211 being a surface orthogonal to the direction of extension of the first groove portion 25 as illustrated in FIG. 11(a) can be an example of a simple configuration for the corner portions 221 and 222 to have a right angle or an acute angle in a plan view. However, the present invention is not limited to the configuration.

FIG. 11(b) illustrates a first claw portion 23B of a first needle support portion 2:1B, which is a further modification of the first needle support portion 21A illustrated in FIG. 11(a). As in the case of the first needle support portion 21A, in the first needle support portion 211B, the corner portions 221 and 222 abutting against the straight needle 51 in the end portion (end portion on the side where the straight needle 51 is inserted) of the first groove portion 25 of the first needle support portion 21B (first claw portion 23B) have an acute angle in a plan view. In addition, in the first needle support portion 21B, the width of the first groove portion 25 is not uniform with respect to the direction of extension of the first groove portion 25 (X-axis direction) and a recess portion 25a is provided inside the corner portions 221 and 222 such that the corner portions 221 and 222 have an acute angle. Also in the first needle support portion 21B (first claw portion 23B), the corner portions 221 and 222 have an acute angle in a plan view as described above, and thus the tissue is fixed at the part of abutting against the straight needle 51 and a movement thereof (movement toward the inside of the first groove portion 25 that follows the straight needle 51 in particular) can be regulated. Accordingly, the tissue can be prevented from, for example, entering the first groove portion 25.

It should be noted that the end surfaces 211 of the first needle support portions 21A and 21B are flat in both FIGS. 11(a) and 11(b) and yet the present invention is not limited to the shape. For example, the corner portions 221 and 222 may be shaped so as to protrude from the end surface 211. In addition, the shape of the first groove portion 25 can be appropriately changed as illustrated in FIG. 11(b). In addition, although a case where the needle-receiving portion is the first needle support portion has been described in FIGS. 11(a) and 11(b), the above effect can be obtained by the second needle support portion having the above structure even in a case where the needle-receiving portion is the second needle support portion as in the automatic needle mover 2.

In addition, the configuration that is illustrated in FIGS. 11(a) and 11(b) is also applicable to an automatic needle mover different in structure from the automatic needle movers 1 to 3. Roughly speaking, the automatic needle movers 1 to 3 have the two shafts extending in the same direction and slidable relative to each other along the longitudinal direction, the needle holding portion provided on one end side of the first shaft, which is one of the shafts, and the needle-receiving portion provided on one end side of the second shaft, which is the other shaft. In addition, the automatic needle movers 1 to 3 have the control portion for controlling the sliding of the two shafts and the control portion is provided on the side opposite to the end side where the needle holding portion and the needle-receiving portion are provided when viewed in the longitudinal direction. By the two shafts being slid under the control of the control portion, the needle holding portion and the needle-receiving portion become close to each other and the straight needle held by the needle holding portion is delivered to the needle-receiving portion. On the other hand, the needle-receiving portion illustrated in FIGS. 11(a) and 11(b) is also applicable to a so-called side opening-type automatic needle mover.

Figure 12:
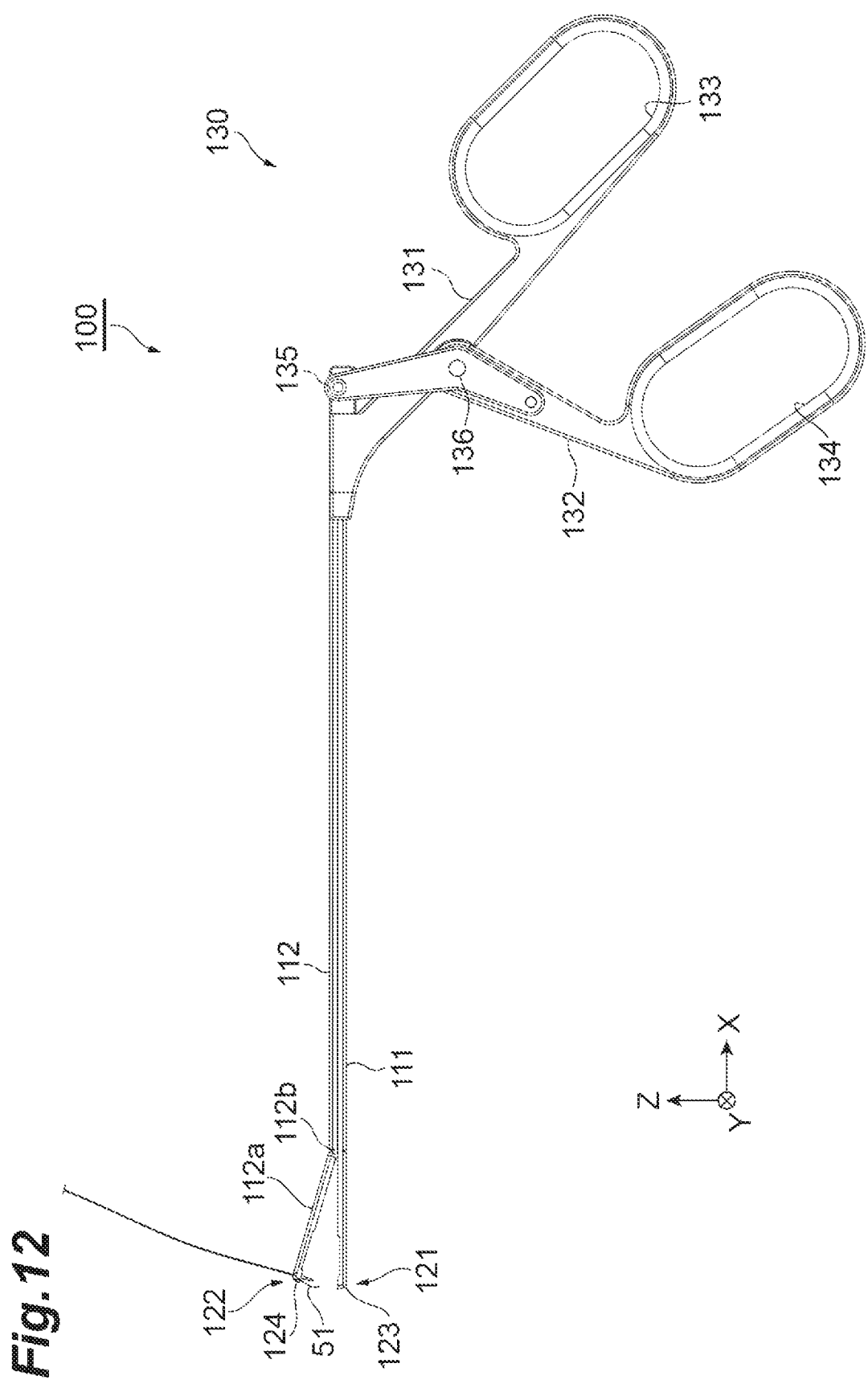
FIG. 12 is a diagram describing a needle mover to which the needle-receiving portion illustrated in FIG. 11 can be applied.

FIG. 12 is a diagram describing a configuration example of a side opening-type automatic needle mover 100. The automatic needle mover 100 has a first shaft 111 having a first needle support portion 121 at the tip thereof and a second shaft 112 having a second needle support portion 122 at the tip thereof. The two shafts, that is, the first shaft 111 and the second shaft 112 extend in the same direction (X-axis direction). A swing arm 112a pivotable with respect to a shaft 12b is provided at the tip of the second shaft 112, and the second needle support portion 122 is provided at the tip of the swing arm 112a.

The first needle support portion 121 protrudes in a direction intersecting the direction of extension of the first shaft 111 (Z-axis positive direction in the case of the automatic needle mover 100). In addition, the second needle support portion 122 protrudes in a direction intersecting the direction of extension of the swing arm 112a of the second shaft 112 and facing the first needle support portion 121 (Z-axis negative direction in a state where the swing arm 112a extends in the X-axis direction in the case of the automatic needle mover 100). As a result, the relative positional relationship between the first needle support portion 121 and the second needle support portion 122 changes as a result of the pivoting of the swing arm 112a.

The automatic needle mover 100 has a handle 130 for pivoting the swing arm 112a with respect to the first shaft 111. The handle 130 includes a first handle 131 and a second handle 132. The first handle 131 is attached to one end side of the first shaft 111 (side opposite to the end portion side where the first needle support portion 121 is provided) and has an opening 133 into which a user of the automatic needle mover 100 inserts a finger in order to operate the first handle 131. In addition, the second handle 132 is pivotably and axially supported by a shaft 135 with respect to one end side of the second shaft 112 (side opposite to the end portion side where the second needle support portion 122 is provided). Further, the second handle 132 is pivotably and axially supported by a shaft 136 with respect to the first handle 131 and has an opening 134 into which the user of the automatic needle mover 100 inserts a linger in order to operate the second handle 132.

In the automatic needle mover 100 described above, the second handle 132 pivots about the shaft 136 when the second handle 132 is operated so as to be separated from the first handle 131. By the second handle 132 being operated so as to be separated from the first handle 131, the end portion of the second handle 132 on the side opposite to the side where the opening 134 is provided (side where the shaft 135 is provided) moves in the X-axis positive direction. As a result, the swing arm 112a pivots about the shaft 112b in the second shaft 112 connected to the second handle 132 via the shaft 135 and the second needle support portion 122 provided at the tip of the swing area 112a becomes close to and is separated from the first needle support portion 121 provided at the tip of the first shaft 111.

On the other hand, the second handle 132 pivots about the shaft 136 when the second handle 132 is operated so as to approach the first handle 131. By the second handle 132 being operated so as to approach the first handle 131, the end portion of the second handle 132 on the side opposite to the side where the opening 134 is provided moves in the X-axis negative direction. As a result, the swing arm 112a pivots about the shaft 112b in the second shaft 112 connected to the second handle 132 via the shaft 135 and the second needle support portion 122 provided at the tip of the swing arm 112a approaches and abuts against the first needle support portion 121 provided at the tip of the first shaft 111.

In a case where the second needle support portion 122 functions as the needle holding portion and the first needle support portion 121 functions as the needle-receiving portion in the automatic needle mover 100 described above, a first claw portion 123 of the first needle support portion 121 is provided with the first groove portion used for delivering the straight needle 51 as in the case of the automatic needle movers 1 to 3 or the like. In addition, a second claw portion 124 of the second needle support portion 122 is provided with the second groove portion used for delivering the straight needle 51 as in the case of the automatic needle movers 1 to 3 or the like. Each of the first groove portion and the second groove portion is provided so as to extend along the direction of extension of the straight needle 51 (Z-axis direction). Further, a needle movement is performed by the straight needle 51 being delivered between the first groove portion and the second groove portion. This point is common to the automatic needle mover 100 and the automatic needle movers 1 to 3.

Here, the corner portions 221 and 222 abutting against the straight needle 51 in the end portion (end portion on the side where the straight needle 51 is inserted) of the first groove portion of the first needle support portion 121 (first claw portion 123) is provided in a case where the first needle support portion 121 is the needle-receiving portion, the tissue is fixed at the part of abutting against the straight needle 51 in a case where the tip of the corner portion has an angle of 90° or an acute angle of less than 90°, and thus a movement thereof (movement toward the inside of the first groove portion that follows the straight needle 51 in particular) can be regulated. Accordingly, the tissue can be prevented from, for example, entering the first groove portion during the needle movement. This effect is not limited to the automatic needle movers 1 to 3 in which the needle is moved by the two shafts sliding in the longitudinal direction, and the same effect can be achieved with the so-called side opening-type automatic needle mover 100 as well. It should be noted that which of the first needle support portion 121 and the second needle support portion 122 is to be used as the needle holding portion and which of the first needle support portion 121 and the second needle support portion 122 is to be used as the needle-receiving portion can be appropriately changed also in the automatic needle mover 100. In addition, the operation mechanism of the side opening-type automatic needle mover 100 is not limited to the above description.

Fifth Embodiment

An automatic needle mover 4 according to a fifth embodiment will be described with reference to FIG. 13. The automatic needle mover 4 differs from the automatic needle movers 1 and 2 in the following points. In other words, the directions of protrusion of the first claw portion 23 of the first needle support portion 21 and the second claw portion 24 of the second needle support portion 22 in the automatic needle movers 1 and 2 and the automatic needle mover 4 are different from each other. In addition, the automatic needle mover 4 differs from the automatic needle movers 1 and 2 in that the first shaft 11 and the second shaft 12 are slidable relative to each other along the longitudinal direction and the sliding directions are different such that the relative position also changes in a direction intersecting the longitudinal direction.

Figure 13:
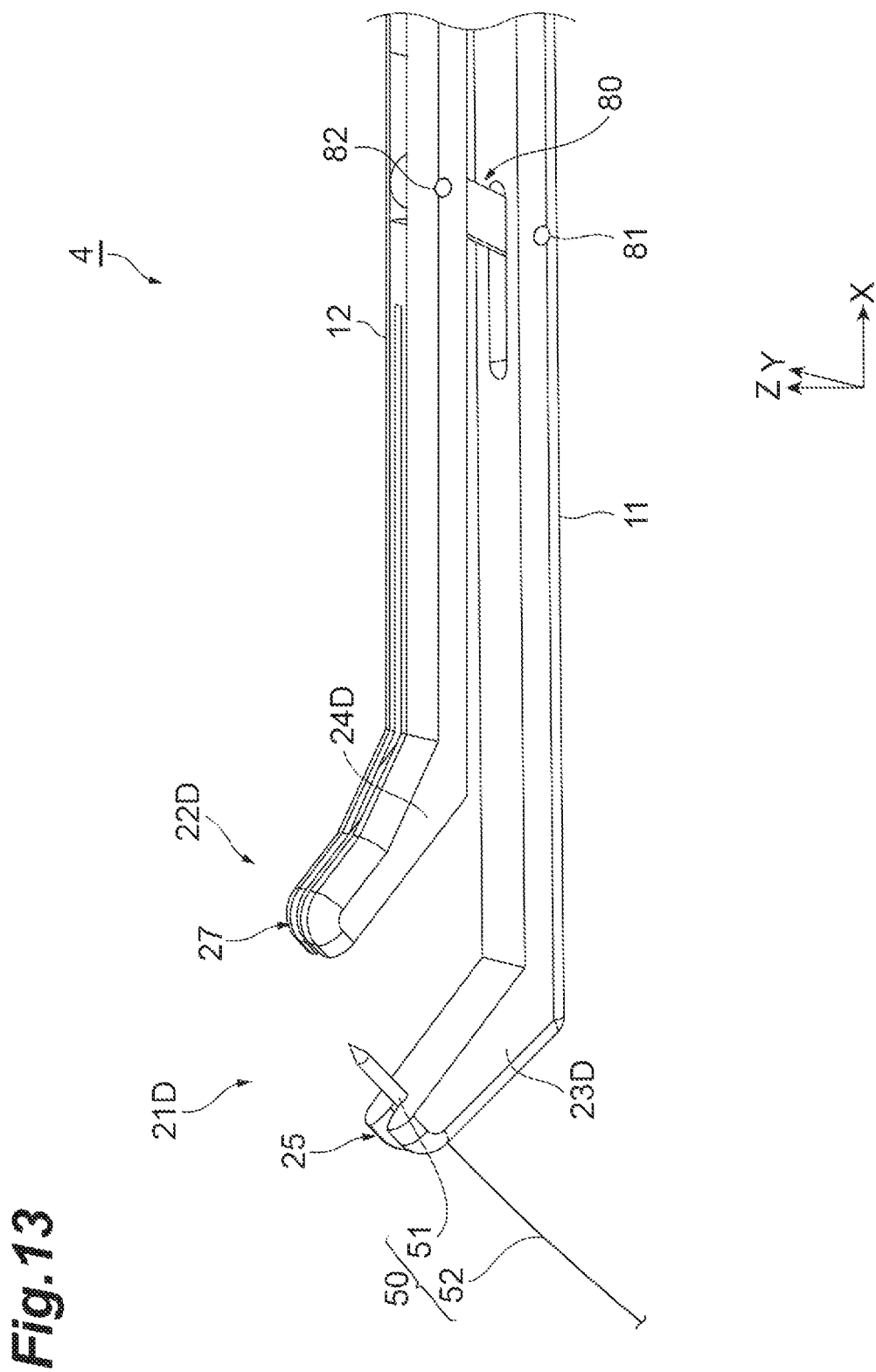
FIG. 13 is a perspective view of the automatic needle mover according to a fifth embodiment.

As illustrated in FIG. 13, the automatic needle mover 4 differs from the automatic needle movers 1 and 2 in that the first shaft 11 and the second shaft 12 are connected by a substantially rod-shaped (long plate-shaped) link member 80 having pivot shafts at both ends thereof. The link member 80 of the automatic needle mover 4 has a first shaft 81 on the first shaft 11 that extends along a direction (Y-axis direction) orthogonal to the direction of extension of the first shaft 11 and the second shaft 12 (X-axis direction) and a second shaft 82 on the second shaft 12 that extends along the direction (Y-axis direction) orthogonal to the direction of extension of the first shaft 11 and the second shaft 12 (X-axis direction). The first shaft 81 and the second shaft 82 are provided at both ends of the link member 80.

The first shaft 11 and the link member 80 are pivotable relative to each other about the first shaft 81 as an axis, and the second shaft 12 and the link member 80 are pivotable relative to each other about the second shaft 82 as an axis. As a result, when the first shaft 11 and the second shaft 12 slide along the longitudinal direction, the link member 80 regulates the direction of the movement. As a result, a configuration is realized in which the distance between the first shaft 11 and the second shaft 12 (distance in the Z-axis direction) changes depending on the direction of extension of the link member 80. It should be noted that the automatic needle mover 4 has a structure in which the movement of the second shaft 12 on the side of the handle 30 functioning as a control portion is not regulated. For example, although a part of the second shaft 12 is connected to the second handle 32 so as to be slidable with respect to the first shaft 11 in a state of being accommodated in the groove portion 37 in the automatic needle mover 1, the structure may be changed in a case where the groove portion 37 interferes with the movement of the second shaft 12 in the up-down direction (Z-axis direction).

In addition, in the automatic needle mover 4, a first claw portion 23D of a first needle support portion 21D and a second claw portion 24D of a second needle support portion 22D protrude from the first shaft 11 and the second shaft 12 in a direction inclined (in the X-axis negative direction) by 45° along the direction of extension of the first shaft 11 and the second shaft 12 (X-axis direction) with respect to the Z-axis positive direction, respectively. In this manner, the directions of protrusion of the first claw portion 23D and the second claw portion 24D in the automatic needle mover 4 are different from those in the automatic needle movers 1 and 2. However, the first groove portion 25 and the second groove portion 27 are formed in the upper end portions of the first claw portion 23D and the second claw portion 24D as in the case of the automatic needle movers 1 and 2. Accordingly, the straight needle 51 is held by the first needle support portion 21D in a state of being inclined by 45° with respect to the direction of extension of the first shaft 11 and the second shaft 12 (X-axis direction) as illustrated in FIG. 13 in a case where, for example, the straight needle 51 is held in the first groove portion 25.

Next, the delivery of the threaded needle 50 (straight needle 51 in particular) in the automatic needle mover 4 will be described with reference to FIG. 14.

Figure 14:
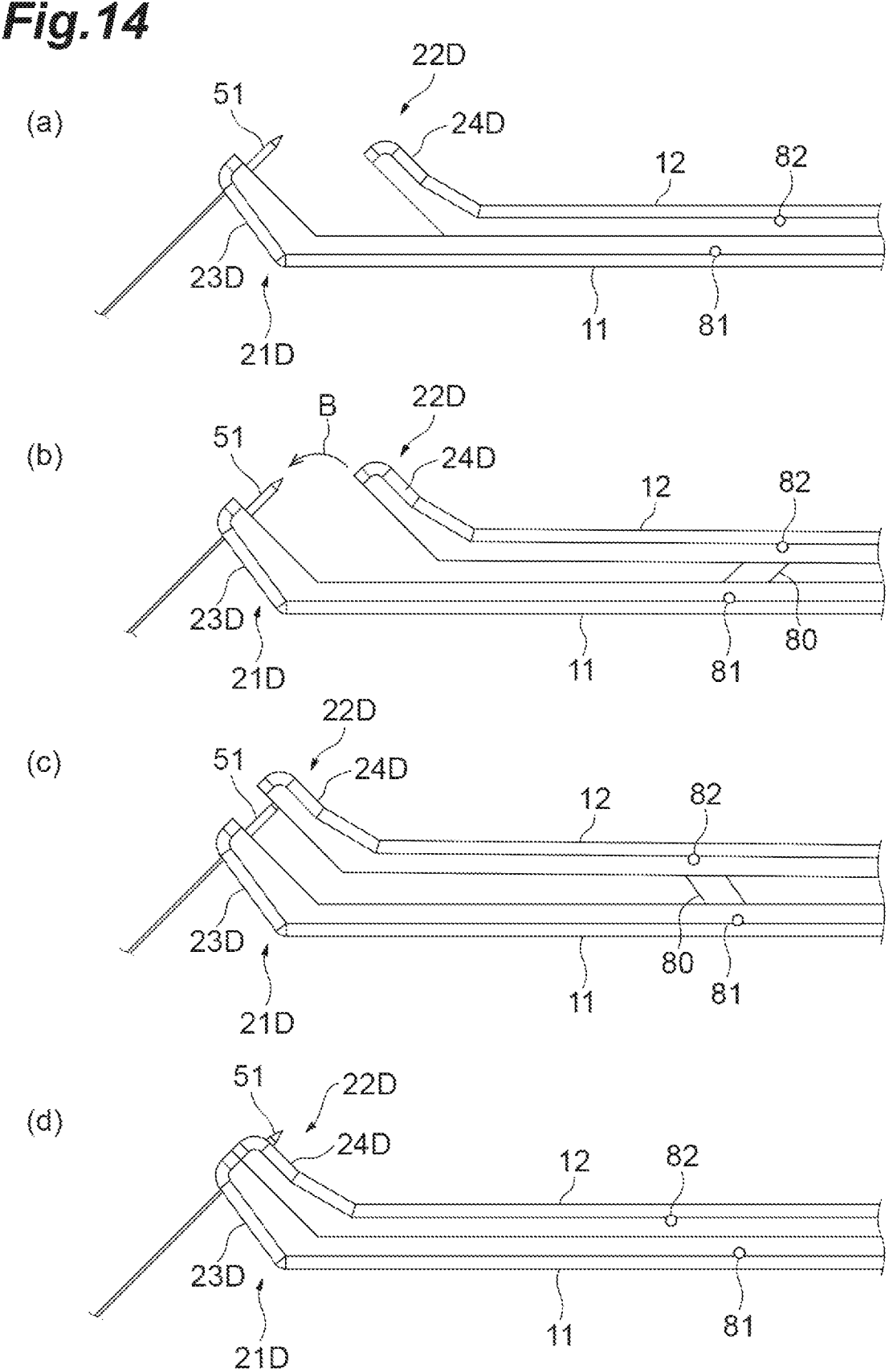
FIG. 14 is a diagram describing threaded needle delivery in the automatic needle mover.

First, as illustrated in FIG. 14(*a*), the first needle support portion 21D and the second needle support portion 22D are separated from each other by the second shaft 12 being slid with respect to the first shaft 11 and the straight needle 51 of the threaded needle 50 is held in a state of being accommodated in the first groove portion 25 of the first needle support portion 21D. The threaded needle 50 is held in the first needle support portion 21D in the same manner as the procedure described in the first embodiment and the like.

Next, the second needle support portion 22D abuts against the first needle support portion 21D as illustrated in FIG. 14(*d*) by the second shaft 12 being slid with respect to the first shaft 11. At this time, the direction of the movement is regulated by the link member 80, and thus the relative positions of the first shaft 11 and the second shaft 12 change such that the link member 80 pivots about the first shaft 81 and the second shaft 82 as axes as illustrated in FIGS. 14(*b*) and 14(*c*). As a result, the second needle support portion 22A of the second shaft 12 approaches the first needle support portion 21A of the first shaft 11 so as to draw a substantially circular arc as indicated by the arrow B in FIG. 14(*b*). As a result, the second needle support portion 22D (second claw portion 24D) becomes close so as to be orthogonal to the direction of extension of the straight needle 51 in the vicinity of the first needle support portion 21D (first claw portion 23D) and the second needle support portion 22D abuts against the first needle support portion 21D as illustrated in FIG. 14(*d*). As a result of this operation, the tip of the straight needle 51 supported by the first groove portion 25 of the first needle support portion 21D is inserted into the second groove portion 27 of the second needle support portion 22D. As a result, the straight needle 51 is held by the second groove portion 27 of the second needle support portion 22D. It should be noted that the second groove portion 27 may be provided with a narrow portion as in the case of the automatic needle movers 1 and 2 described above. In addition, the corner portion may form a right or acute angle as in the fourth embodiment.

Subsequently, the straight needle 51 is held by the second needle support portion 22D by the second shaft 12 being slid with respect to the first shaft 11 and the first needle support portion 21D and the second needle support portion 22D being separated from each other. In other words, the straight needle 51 is delivered from the first needle support portion 21D to the second needle support portion 22D.

Although the delivery of the straight needle 51 in the automatic needle mover 4 has been outlined above, the procedure for delivering the straight needle 51 is the same as those in the automatic needle movers 1 and 2. However, the direction of movement of the straight needle can be changed from the direction of extension of the first shaft 11 and the second shaft 12 (X-axis direction) by the directions of protrusion of the first claw portion 23D and the second claw portion 24D being inclined with respect to the Z-axis direction as in the automatic needle mover 4 and the direction of movement of the second shaft 12 being regulated with respect to the first shaft 11 by means of the link member 80. It should be noted that the direction of movement of the second shaft 12 (shape of the substantially circular arc drawn during the sliding) can be controlled with respect to the first shaft 11 by the attachment position of the link member 80 and the size of the link member 80. When the straight needle 51 is delivered, the first claw portion 23D (first needle support portion 21D) and the second claw portion 24D (second needle support portion 22D) move in the same direction as the direction of extension of the straight needle 51, and thus the straight needle 51 can be appropriately delivered. Accordingly the direction of movement of the second shaft 12 (shape of the substantially circular arc drawn during the sliding) can be designed with respect to the first shaft 11 with the positional relationship between the first claw portion 23D and the second claw portion 24D during the delivery of the straight needle 51 taken into account. It should be noted that the substantially circular arc shape is a shape similar to a circular arc. The path of movement that is generated by the change in the relative positions of the first shaft 11 and the second shaft 12 connected by the link member 80 is referred to as "substantially circular arc" and is not limited to a strictly circular arc.

As described above, in the automatic needle mover 4, the second needle support portion 22D functioning as the needle-receiving portion can be moved in a substantially circular arc-shaped trajectory with respect to the first needle support portion 21D functioning as the needle holding portion. Accordingly, even if the direction of extension of the straight needle 51 supported in the needle holding portion is different from, for example, the longitudinal direction of the two shafts as described in the above embodiment, the needle-receiving portion can be moved in accordance with the direction of the straight needle 51 and the straight needle 51 can be moved. In addition, in the automatic needle mover 4 described above, the first claw portion 23D and the second claw portion 24D are inclined by 45° with respect to the longitudinal direction of the two shafts and the straight needle 51 is also supported in a state of being inclined by 45° with respect to the longitudinal direction of the two shafts. Even in such a state, the delivery from the needle holding portion to the needle-receiving portion can be appropriately performed and the straight needle 51 can be moved by the link member 80 being provided.

It should be noted that a case where the first needle support portion 21D has a function as the needle holding portion and the second needle support portion 22D has a function as the needle-receiving portion in the automatic needle mover 4 has been described and yet these functions may be reversed. Even in that case, the needle-receiving portion draws a substantially circular arc-shaped trajectory with respect to the needle holding portion by the link member 80 being used. Accordingly, the straight needle 51 inclined by 45° with respect to the longitudinal direction of the two shafts can be delivered as in the automatic needle mover 4 described above. It should be noted that this angle is not particularly limited although the inclination angle of the straight needle 51 is 45° as an example in the automatic needle mover 4.

Figure 15:
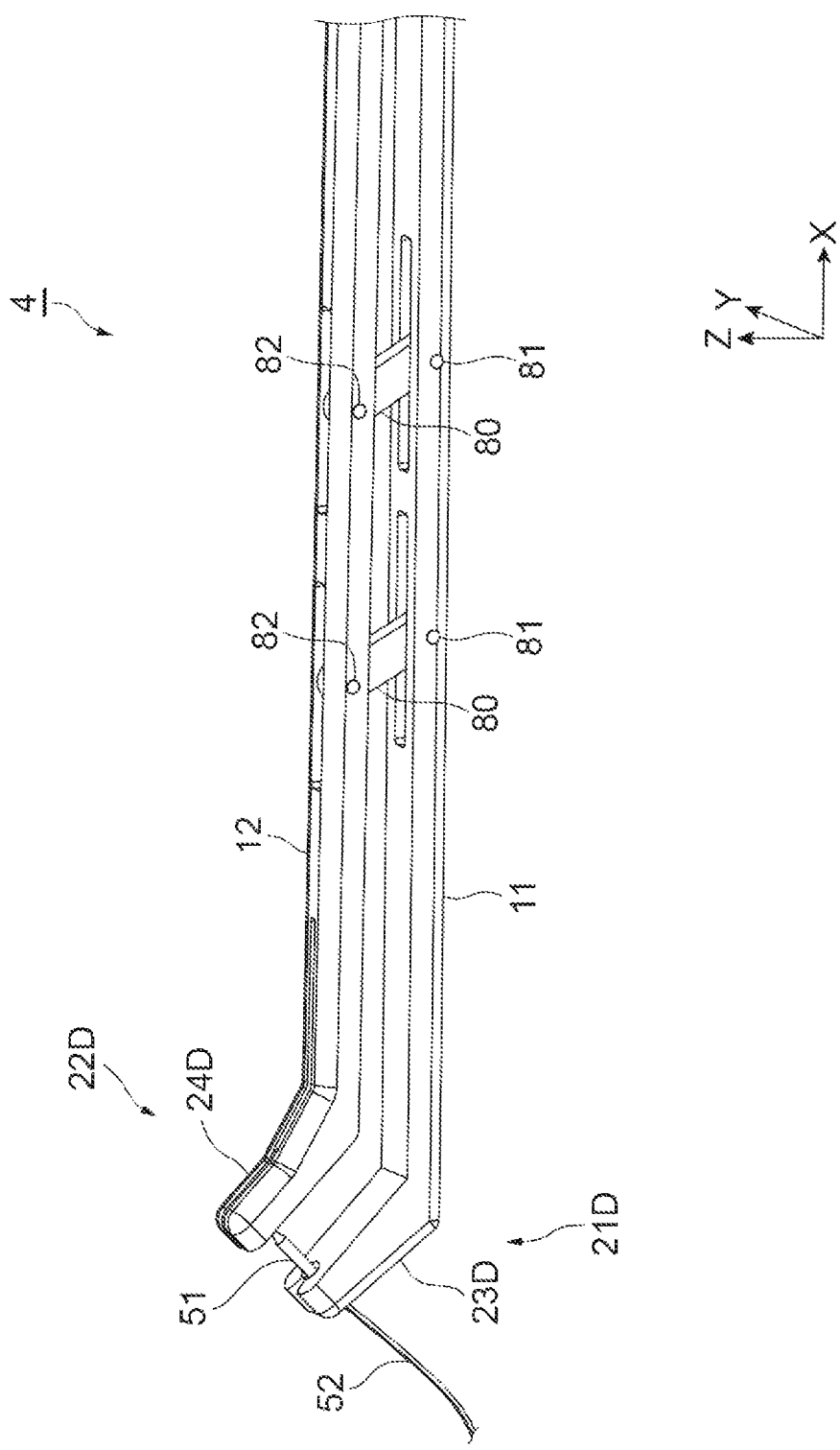
FIG. 15 is a diagram describing a modification example of the automatic needle mover according to the fifth embodiment.

FIG. 15, which is a modification example of the automatic needle mover 4, illustrates an example in which two link members 80 are provided. In the automatic needle mover 4, the second needle support portion 22D of the second shaft 12 may approach or be separated from the first needle support portion 21D of the first shaft 11 so as to draw a substantially circular arc. The above configuration can be realized even in a case where a plurality of the link members 80 having the same shape are provided between the first shaft 11 and the second shaft 12. Accordingly, two or more link members 80 may be provided so that the load on the link member 80 and the vicinity thereof is dispersed. In addition, a plurality of link members having different shapes may be provided depending on the design.

Although the embodiments of the present invention have been described above, the present invention is not limited to the above-described embodiments and various modifications can be made.

For example, the shape of the first shaft 11, the shape of the second shaft 12, the shape of the handle 30, and the like can be appropriately changed. In addition, the shape of the needle holding portion, the shape of the needle-receiving portion, the shapes of the claw portions (first and second claw portions) where the needle holding portion and the needle-receiving portion are provided, and the like can be appropriately changed.

REFERENCE SIGNS LIST 1, 2, 3, 4: automatic needle mover, 11: first shaft, 12: second shaft, 13, 33, 34: opening, 14: protrusion, 21, 21A, 21B, 21D: first needle support portion, 22, 22D: second needle support portion, 23, 23A, 23B, 23D: first claw portion, 24, 24D: second claw portion, 25: first groove portion, 26: narrow portion, 27: second groove portion, 28: first region, 29: second region, 30: handle, 31: first handle, 32: second handle, 35, 36: shaft, 37, 64, 66: groove portion, 50: threaded needle, 51: straight needle, 52: thread, 60: shaft portion, 61: needle holding portion, 62: needle-receiving portion, 63, 65: claw portion, 67: hook, 68: pivot shaft, 70: control unit, 71, 73: operation lever, 80: link member, 81: first shaft, 82: second shaft.

The invention claimed is:

1. An automatic needle mover for moving a medical threaded needle including a straight needle and a thread connected to the straight needle, the automatic needle mover comprising:
    two shafts extending in a same direction and slidable relative to each other along a longitudinal direction;
    a needle-holding portion provided on one end side of a first shaft as one of the two shafts;
    a needle-receiving portion provided on one end side of a second shaft as the other shaft of the two shafts; and
    a control portion for controlling the sliding of the two shafts, the control portion being provided on a side opposite the needle-holding portion and the needle-receiving portion when viewed in the longitudinal direction,
    wherein the needle-holding portion has a first claw portion protruding in a direction intersecting the longitudinal direction of the first shaft in an end portion of the first shaft and a first groove portion provided in the first claw portion and including a region having a width smaller than a diameter of the straight needle and larger than a diameter of the thread,
    the needle-receiving portion has a second claw portion protruding in a direction intersecting the longitudinal direction of the second shaft in an end portion of the second shaft and a second groove portion provided in the second claw portion and having a width at which the straight needle can be inserted by elasticity of the second claw portion and the straight needle can be held by friction with the straight needle when the straight needle is inserted along the longitudinal direction, and
    the needle-holding portion and the needle-receiving portion become close to each other and the straight needle held by the needle-holding portion can be press-fitted into the needle-receiving portion as a result of the sliding of the two shafts.

2. The automatic needle mover according to claim 1, wherein the needle-receiving portion is farther from the control portion than the needle-holding portion along the longitudinal direction of the two shafts.

3. The automatic needle mover according to claim 2, wherein the second groove portion has a narrow portion when viewed along the longitudinal direction.

4. The automatic needle mover according to claim 1, wherein the needle-receiving portion is closer to the control portion than the needle-holding portion along the longitudinal direction of the two shafts.

5. The automatic needle mover according to claim 1, wherein the needle-receiving portion has a pair of corner portions formed by an end surface of the second claw portion on a side where the straight needle is inserted, an angle of the end surface abutting against the straight needle being 90° or an acute angle in a plan view.

6. The automatic needle mover according to claim 1, wherein the two shafts are connected by a link member provided at both ends with a third shaft serving as an axis for pivoting with respect to the first shaft and a fourth shaft serving as an axis for pivoting with respect to the second shaft, and the needle-receiving portion moves in a substantially circular arc-shaped trajectory with respect to the needle-holding portion as a result of the sliding of the first shaft and the second shaft.

7. The automatic needle mover according to claim 1, wherein the needle-receiving portion and the needle-holding portion are pivotable about a pivot shaft as an axis, the pivot shaft being provided in the end portions of the two shafts on a side where the needle-receiving portion and the needle-holding portion are provided and extending in a direction intersecting the longitudinal direction, and a positional relationship between the needle-receiving portion and the needle-holding portion along the longitudinal direction of the two shafts is reversed as a result of the pivoting about the pivot shaft as an axis.

* * * * *